(12) United States Patent
Kuroda et al.

(10) Patent No.: US 10,180,382 B2
(45) Date of Patent: Jan. 15, 2019

(54) VISCOELASTICITY MEASUREMENT METHOD AND VISCOELASTICITY MEASUREMENT DEVICE

(71) Applicant: NATIONAL INSTITUTE OF ADVANCED INDUSTRIAL SCIENCE AND TECHNOLOGY, Chiyoda-ku, Tokyo (JP)

(72) Inventors: Masaharu Kuroda, Ibaraki (JP); Yasuyuki Yamamoto, Ibaraki (JP); Hiroshi Yabuno, Kanagawa (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 1206 days.

(21) Appl. No.: 14/374,783

(22) PCT Filed: Jan. 25, 2013

(86) PCT No.: PCT/JP2013/000406
§ 371 (c)(1),
(2) Date: Oct. 1, 2014

(87) PCT Pub. No.: WO2013/111608
PCT Pub. Date: Aug. 1, 2013

(65) Prior Publication Data
US 2015/0094964 A1    Apr. 2, 2015

(30) Foreign Application Priority Data

Jan. 27, 2012   (JP) .................................. 2012-015801
Jan. 27, 2012   (JP) .................................. 2012-015802
Jan. 27, 2012   (JP) .................................. 2012-015803

(51) Int. Cl.
*G01N 11/16*    (2006.01)
*G01N 3/08*     (2006.01)

(52) U.S. Cl.
CPC ............... *G01N 11/16* (2013.01); *G01N 3/08* (2013.01); *G01N 2203/0094* (2013.01)

(58) Field of Classification Search
CPC ... G01N 3/08; G01N 11/16; G01N 2203/0094
See application file for complete search history.

(56) References Cited

U.S. PATENT DOCUMENTS 5,766,137 A     6/1998  Omata
5,777,232 A *   7/1998  Kurita ..................... G05D 19/02
                                                  198/750.1

(Continued)

FOREIGN PATENT DOCUMENTS

JP     H11-118689 A    4/1999
JP     2004-361300 A   12/2004
WO     2011/086879 A1  7/2011

OTHER PUBLICATIONS

Kurita et al., "Measurement of Dynamic Stiffness of Subcutaneous Tissues Using Self-Excited Vibration Generated by Positive Feedback of Velocity," Department of Mechanical Systems Engineering, University of Shiga Prefecture, No. 04-0161. pp. 2573-2579 (Sep. 2004).

(Continued)

*Primary Examiner* — Mohamed Charioui
(74) *Attorney, Agent, or Firm* — Young Basile Hanlon & MacFarlane, P.C.

(57) ABSTRACT

A linear elastic modulus measurement method and a linear elastic modulus measurement device can reduce external disturbances such as oscillation and electrical noise, and accurately and stably measure the linear elastic modulus of a linear elastic body even in the case where damping due to viscous stress is large. The measurement device computes the oscillation velocity (dx/dt) of an oscillator from the displacement of the oscillator brought into contact with the linear elastic body, and multiplies dx/dt by a linear velocity (Continued)

feedback gain to generate a feedback control signal. The measurement device applies, to the oscillator, a force proportional to the oscillation velocity of the oscillator by the feedback control signal, to cause the oscillator to self-oscillate. The measurement device computes the linear elastic modulus of the linear elastic body from the frequency when the self-oscillation of the oscillator is detected and the mass of the oscillator.

6 Claims, 12 Drawing Sheets

(56) References Cited

U.S. PATENT DOCUMENTS

| | | | | |
|---|---|---|---|---|
| 2005/0097964 A1* | 5/2005 | Fujii | ............... | G01B 11/161 |
| | | | | 73/778 |
| 2005/0267695 A1* | 12/2005 | German | ............... | G01N 3/30 |
| | | | | 702/41 |
| 2007/0157698 A1* | 7/2007 | Allaire | ............... | G01N 3/34 |
| | | | | 73/12.01 |
| 2012/0291528 A1 | 11/2012 | Kuroda et al. | | |

OTHER PUBLICATIONS

JPO Office Action dated Oct. 13, 2015 for the corresponding Japanese Patent Application No. 2012-015801.

Horigome, et al., "Viscosity Measurement in High Frequency Range with New Rheometer Based on Mechanical Impedance Analysis," Nihon Reoroji Gakkaishi, vol. 29, No. 1 (The Society of Rheology, Japan 2001), pp. 21-25.

Aono, et al., "Proposition of Self-Excited Oscillation Type Viscometer," Dynamics and Design Conference 2010, No. 10-8 (print out from CD-ROM), 5 pages.

Mitani Yukinori, "Measurement Technology for Young's Modulus," IIC Review/2010/4, No. 43 (IHI Inspection & Instrumentation Co., Ltd. 2010), pp. 30-34.

PCT Notification of Transmittal of Translation of the International Preliminary Report on Patentability, dated Aug. 7, 2014.

* cited by examiner

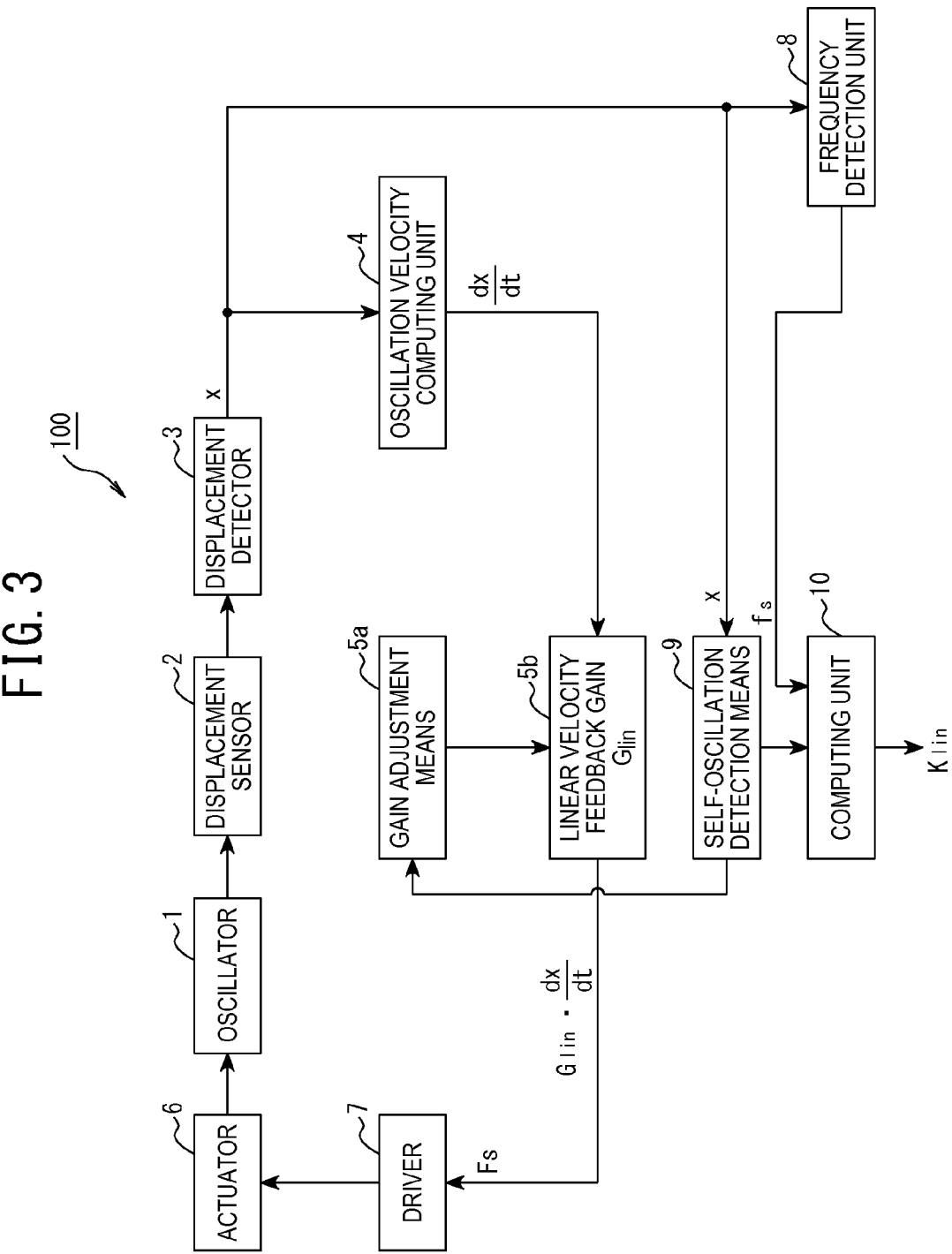

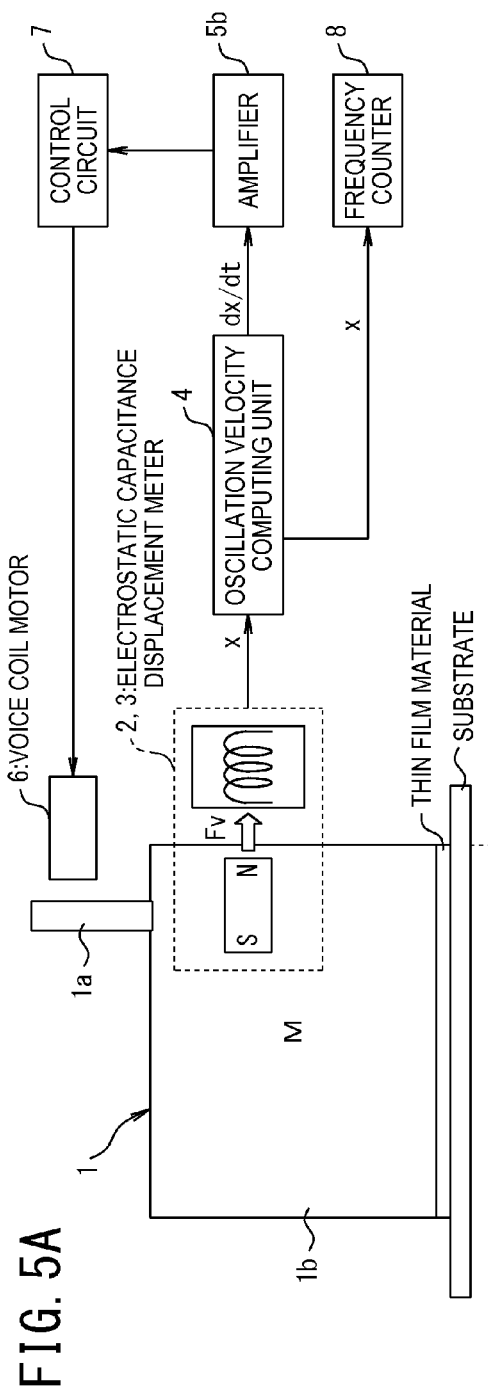
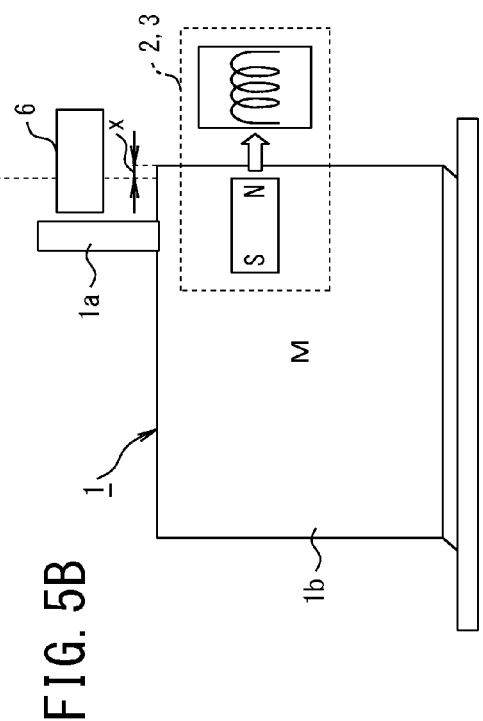
FIG. 5A
FIG. 5B

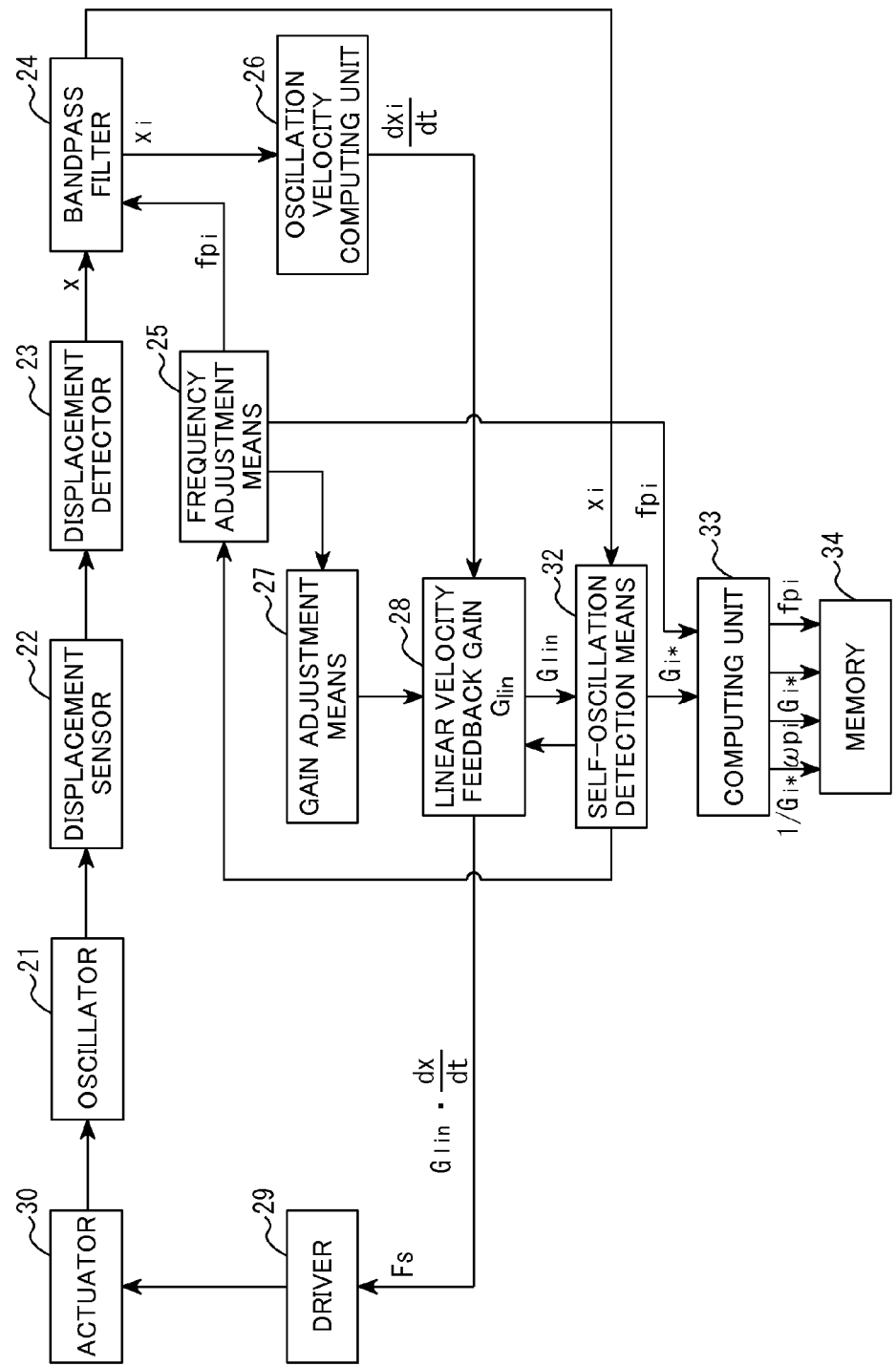

VISCOELASTICITY MEASUREMENT METHOD AND VISCOELASTICITY MEASUREMENT DEVICE

CROSS-REFERENCES TO RELATED APPLICATIONS

This application claims priority to Japanese Patent Application No. P2012-15801, filed Jan. 27, 2012, Japanese Patent Application No. P2012-15802, filed Jan. 27, 2012, and Japanese Patent Application No. P2012-15803, filed Jan. 27, 2012, each of which is incorporated herein in its entirety by reference.

TECHNICAL FIELD

The present invention relates to techniques of measuring the elastic modulus of a linear elastic body, and more particularly to a linear elastic modulus measurement method and a linear elastic modulus measurement device that are effective in reducing the influence of damping due to viscous stress in a mechanical system in which viscous stress occurs with elastic force.

The present invention also relates to methods of measuring the properties of a viscoelastic body, and more particularly to a viscoelasticity measurement method and a viscoelasticity measurement device that are effective in estimating the internal properties of a viscoelastic body while clearly distinguishing elasticity and viscosity in the case where the viscoelastic body has complex viscoelasticity unable to be represented by a simple mechanical model.

The present invention further relates to techniques of measuring the linear elasticity, nonlinear elasticity, linear viscosity, and nonlinear viscosity of a measurement object using a self-oscillator.

BACKGROUND

Conventionally known methods of measuring the elastic modulus of a linear elastic body include: a method of applying static strain to an elastic body and measuring the stress to compute the elastic modulus; and a method of applying forced oscillation to a linear elastic body and computing the elastic modulus from the resonance frequency. These measurement methods are described in, for example, IIC REVIEW/2010/4, No. 43 P30-34 (IHI Inspection & Instrumentation Co., Ltd.).

Conventionally known methods of measuring the viscoelasticity of a viscoelastic body include a method of applying forced oscillatory displacement to a viscoelastic body and measuring the resulting stress or applying forced oscillatory stress to a viscoelastic body and measuring the resulting displacement to measure the viscoelasticity (for example, see IIC REVIEW/2010/4. No. 43 P30-34 (IHI Inspection & Instrumentation Co., Ltd.)). A rheometer is an instrument for measuring the viscoelasticity of a viscoelastic body using such a method. Types of rheometers include a cone and plate rheometer and a coaxial double cylinder rheometer, depending on the oscillator shape.

These rheometers apply shear deformation to a viscoelastic body sandwiched between an oscillator and a stationary object and measure the shear stress to measure the viscoelasticity, or apply shear stress to the viscoelastic body and measure the shear deformation to measure the viscoelasticity such as relaxation time, dynamic elastic modulus, and loss elastic modulus.

In the case where the viscoelastic body has complex viscoelasticity unable to be represented by a simple mechanical model, it is assumed that the viscoelastic body includes a plurality of spring elements and a plurality of viscous elements, and has a plurality of relaxation times. In such a case, the frequency spectrum of each of the dynamic elastic modulus and the loss elastic modulus is formed by superimposing the waveforms deriving from the plurality of relaxation times.

Viscometers for measuring the viscosity of a measurement object such as a fluid, for example, have conventionally been classified roughly into (1) capillary, (2) falling sphere, (3) rotational, (4) chemical, and (5) oscillatory, depending on the basic principle.

Of these, the following oscillatory viscometers have been proposed: a viscometer that determines the viscosity of a measurement object from the drive current when a sensitive plate is caused to electromagnetically oscillate in the measurement object at a predetermined amplitude (for example, see IIC REVIEW/2010/4. No. 43 P30-34 (IHI Inspection & Instrumentation Co., Ltd.)); and a viscometer that forces an oscillator to oscillate, obtains a frequency response curve indicating the correspondence between the oscillation frequency and the oscillation amplitude of the oscillator, and determines the viscosity from its Q factor.

Known methods of measuring the elastic modulus of a measurement object include: a method of applying static strain to a measurement object and measuring the stress to compute the elastic modulus; and a method of applying forced oscillation to a measurement object and computing the elastic modulus from the resonance frequency. These measurement methods are described in, for example, Nihon Reoroji Gakkaishi (Journal of the Society of Rheology, Japan), Vol. 29, No. 1 (2001), pp. 21-25.

BRIEF SUMMARY

Of the above-mentioned conventional techniques, the method of applying static strain to an elastic body and measuring the stress to compute the elastic modulus is susceptible to external disturbances such as oscillation and electrical noise, and has difficulty in achieving accurate and stable measurement. In particular, the method is not suitable for viscoelastic bodies.

The method of applying forced oscillation and computing the elastic modulus from the resonance frequency has difficulty in accurately determining the resonance frequency because, especially in the case where damping due to viscous stress is large, the power spectrum near the resonance frequency expands and its peak is blurred or no peak appears.

The conventional rheometer estimates, in the case where a viscoelastic body has complex viscoelasticity, the viscoelasticity of the viscoelastic body from the frequency spectrum formed by superimposing the waveforms deriving from the plurality of relaxation times. If the elastic moduli are small or the relaxation times are close to each other, however, the conventional rheometer has difficulty in clearly distinguishing between them.

Of the above-mentioned conventional techniques, the method of measuring the viscosity using the frequency response curve needs to sweep the oscillation frequency in a wide frequency range, and so requires considerable effort to obtain the frequency response curve.

The method of applying static strain to a measurement object and measuring the stress to compute the elastic modulus is susceptible to external disturbances such as oscillation and electrical noise, and has difficulty in achieving accurate and stable measurement. In particular, the method is not suitable for viscoelastic bodies.

The method of applying forced oscillation and computing the viscosity from the resonance frequency and the Q factor has difficulty in accurately determining the resonance frequency and the Q factor because, especially in the case where damping due to viscous stress is large, the power spectrum near the resonance frequency expands and its peak is blurred or no peak appears.

The present invention has a first object of solving the above-mentioned problem with the method of measuring the elastic modulus of a linear elastic body, and providing a linear elastic modulus measurement method and a linear elastic modulus measurement device that are not susceptible to external disturbances such as oscillation and electrical noise and can accurately and stably measure the linear elastic modulus even in the case where damping due to viscous stress is large.

The present invention also has a second object of solving the above-mentioned problem with the method of measuring the properties of a viscoelastic body, and providing a viscoelasticity measurement method and a viscoelasticity measurement device that are effective in estimating the internal properties of a viscoelastic body while clearly distinguishing elasticity and viscosity especially in the case where the viscoelastic body has complex viscoelasticity unable to be represented by a simple mechanical model.

The present invention also has a third object of providing a viscoelasticity measurement method and a viscoelasticity measurement device that can measure not only linear viscosity and linear elasticity but also nonlinear viscosity and nonlinear elasticity by causing an oscillator to self-oscillate through feedback control using both linear velocity feedback and nonlinear feedback.

[Mode 1] To achieve the objects stated above, a linear elastic modulus measurement method according to mode 1 is a linear elastic modulus measurement method using a linear elastic modulus measurement device that includes: an oscillator that is brought into contact with a measurement object; an actuator for causing the oscillator to self-oscillate; an oscillation velocity detection unit for detecting an oscillation velocity of the oscillator; and a feedback control unit for positively feeding back the oscillation velocity detected by the oscillation velocity detection unit, to feedback-control the actuator by a feedback control signal defined as $$Fs = G_{lin} \cdot (dx/dt)$$

where Fs is the feedback control signal, $G_{lin}$ is a linear velocity feedback gain which is a positive value, and $dx/dt$ is the oscillation velocity of the oscillator. The linear elastic modulus measurement method includes: a step of changing the linear velocity feedback gain in the feedback control; a step of detecting whether or not the oscillator is self-oscillating; and a step of computing a linear elastic modulus of the measurement object, based on an oscillation frequency when self-oscillating of the oscillator is detected.

[Mode 2] A linear elastic modulus measurement method according to mode 2 is the structure according to mode 1, wherein in the step of computing the linear elastic modulus, a linear elastic modulus $K_{lin}$ of the measurement object is computed by $K_{lin} = \omega_s^2 \times M$, where $\omega_s = 2\pi \times f_s$, M is a mass of the oscillator and $f_s$ is an oscillation frequency of the oscillator, and wherein the oscillation frequency when self-oscillating of the oscillator is detected is used as the oscillation frequency $f_s$.

[Mode 3] A linear elastic modulus measurement method according to mode 3 is the structure according to mode 1 or 2, wherein the linear elastic modulus measurement device includes a displacement detection unit for detecting the displacement x of the oscillator, and wherein the linear elastic modulus measurement method includes a step of preliminarily causing the oscillator to oscillate at a constant frequency, in the case where the displacement x in an initial stage when the oscillator starts self-oscillation is less than a detection lower limit of the displacement detection unit.

[Mode 4] To achieve the objects stated above, a linear elastic modulus measurement device according to mode 4 is a linear elastic modulus measurement device including: an oscillator that is brought into contact with a measurement object; an actuator for causing the oscillator to self-oscillate; an oscillation velocity detection unit for detecting an oscillation velocity of the oscillator; a feedback control unit for positively feeding back the oscillation velocity detected by the oscillation velocity detection unit, to feedback-control the actuator by a feedback control signal defined as $$Fs = G_{lin} \cdot (dx/dt)$$

where Fs is the feedback control signal, $G_{lin}$ is a linear velocity feedback gain, which is a positive value, and $dx/dt$ is the oscillation velocity of the oscillator; a gain adjustment unit for changing the linear velocity feedback gain in the feedback control; a self-oscillation detection unit for detecting whether or not the oscillator is self-oscillating; and a linear elastic modulus computing unit for computing a linear elastic modulus of the measurement object, based on an oscillation frequency when the self-oscillation detection unit determines that self-oscillating of the oscillator is detected.

With such a structure, the oscillation velocity detection unit detects the oscillation velocity $dx/dt$ of the oscillator, and the feedback control unit feedback-controls the actuator by the feedback control signal $F_s = G_{lin} \cdot (dx/dt)$ obtained by multiplying the detected oscillation velocity $dx/dt$ by the linear velocity feedback gain $G_{lin}$. When feedback-controlled, the actuator applies a force proportional to the oscillation velocity of the oscillator to the oscillator in contact with the measurement object. The gain adjustment unit changes the linear velocity feedback gain, and the self-oscillation detection unit detects whether or not the oscillator is self-oscillating. In the case where the self-oscillation detection unit detects that the oscillator is self-oscillating, the linear elastic modulus computing unit computes the linear elastic modulus of the measurement object based on the oscillation frequency when the self-oscillation is detected.

[Mode 5] To achieve the objects stated above, a viscoelasticity measurement method according to mode 5 is a viscoelasticity measurement method for a measurement object using a viscoelasticity measurement device that includes: an oscillator that is brought into contact with the measurement object; an actuator for causing the oscillator to self-oscillate; a displacement sensor for detecting an oscillation displacement of the oscillator; a specific frequency component extraction unit for extracting a signal component of a specific frequency from a displacement signal output from the displacement sensor; an oscillation velocity detection unit for detecting an oscillation velocity of the oscillator, based on the signal component of the specific frequency extracted by the specific frequency component extraction unit; and a feedback control unit for positively feeding back the oscillation velocity detected by the oscillation velocity detection unit to feedback-control the actuator by a feedback control signal defined as $$Fs = G_{lin} \cdot (dx/dt)$$

where Fs is the feedback control signal, $G_{lin}$ is a linear velocity feedback gain which is a positive value, x is a displacement of the oscillator, and dx/dt is the oscillation velocity of the oscillator. The viscoelasticity measurement method includes: a step of changing the specific frequency used when the specific frequency component extraction unit extracts the signal component; a step of changing the linear velocity feedback gain in the feedback control, for the changed specific frequency; a step of detecting whether or not the oscillator is self-oscillating each time the feedback control using the changed linear velocity feedback gain is performed; and a step of measuring the linear velocity feedback gain when self-oscillating of the oscillator is detected.

[Mode 6] A viscoelasticity measurement method according to mode 6 is the structure according to mode 5, further including a step of generating a frequency spectrum of viscoelasticity indicating a relation between an inverse of the linear velocity feedback gain and an oscillation angular frequency corresponding to each specific frequency when self-oscillating of the oscillator is detected.

[Mode 7] A viscoelasticity measurement method according to mode 7 is the structure according to mode 5 or 6, wherein the specific frequency component extraction unit includes a bandpass filter.

[Mode 8] To achieve the objects stated above, a viscoelasticity measurement device according to mode 8 is a viscoelasticity measurement device including: an oscillator that is brought into contact with a measurement object; an actuator for causing the oscillator to self-oscillate; a displacement sensor for detecting an oscillation displacement of the oscillator; a specific frequency component extraction unit for extracting a signal component of a specific frequency from a displacement signal output from the displacement sensor; an oscillation velocity detection unit for detecting an oscillation velocity of the oscillator based on a displacement signal component of the specific frequency extracted by the specific frequency component extraction unit; a feedback control unit for positively feeding back the oscillation velocity detected by the oscillation velocity detection unit to feedback-control the actuator by a feedback control signal defined as $$Fs = G_{lin} \cdot (dx/dt)$$

where Fs is the feedback control signal, $G_{lin}$ is a linear velocity feedback gain, which is a positive value, x is a displacement of the oscillator, and dx/dt is the oscillation velocity of the oscillator; a specific frequency adjustment unit for changing the specific frequency used when the specific frequency component extraction unit extracts the signal component; a gain adjustment unit for changing the linear velocity feedback gain in the feedback control, for the changed specific frequency; a self-oscillation detection unit for detecting whether or not the oscillator is self-oscillating each time the feedback control using the changed linear velocity feedback gain is performed; and a viscoelasticity measurement unit for measuring the linear velocity feedback gain when self-oscillating of the oscillator is detected.

With such a structure, when the displacement sensor detects the displacement of the oscillator, the specific frequency component extraction unit extracts the signal component of the specific frequency from the output signal of the displacement sensor, and the oscillation velocity detection unit detects the oscillation velocity of the oscillator based on the signal component of the specific frequency. The feedback control unit feedback-controls the actuator by the feedback control signal obtained by multiplying the oscillation velocity corresponding to the specific frequency by the linear velocity feedback gain. When feedback-controlled, the actuator applies a force proportional to the oscillation velocity of the oscillator to the oscillator in contact with the measurement object. When the specific frequency adjustment unit changes the specific frequency used to extract the signal component, the gain adjustment unit changes the linear velocity feedback gain for the changed specific frequency. The self-oscillation detection unit detects whether or not the oscillator is self-oscillating each time the feedback control using the changed linear velocity feedback gain is performed. In the case where the self-oscillation detection unit detects that the oscillator is self-oscillating, the viscoelasticity measurement unit measures the linear velocity feedback gain when the self-oscillation is detected.

[Mode 9] To achieve the objects stated above, a viscoelasticity measurement method according to mode 9 is a viscoelasticity measurement method for a measurement object using a viscoelasticity measurement device that includes: an oscillator that is brought into contact with the measurement object; an actuator for causing the oscillator to self-oscillate; an oscillation velocity detection unit for detecting an oscillation velocity of the oscillator; and a feedback control unit for, using the oscillation velocity detected by the oscillation velocity detection unit, driving and feedback-controlling the actuator by a feedback control signal defined as $$Fb = (G_{lin} - G_{non} \cdot x^2) \cdot (dx/dt) \quad (1)$$

where Fb is the feedback control signal, $G_{lin}$ is a linear velocity feedback gain which is a positive value, $G_{non}$ is a nonlinear feedback gain which is a positive value, x is a displacement of the oscillator, and dx/dt is the oscillation velocity of the oscillator. The viscoelasticity measurement method includes: a gain adjustment step of selectively changing one of the linear velocity feedback gain and the nonlinear feedback gain in the feedback control; a physical quantity measurement step of measuring a physical quantity relating to oscillation of the oscillator when one of the linear velocity feedback gain and the nonlinear feedback gain is changed in the gain adjustment step; and a viscoelasticity computing step of computing a linear viscosity, a nonlinear viscosity, a linear elastic modulus, and a nonlinear elastic modulus of the measurement object, based on an equation that holds true with the physical quantity measured in the physical quantity measurement step, a mechanical model of modeling elasticity and damping of the oscillator, a mechanical model of modeling linear viscosity, nonlinear viscosity, linear elasticity, nonlinear elasticity of the measurement object and the expression (1).

[Mode 10] A viscoelasticity measurement method according to mode 10 is the structure according to mode 9, wherein in the viscoelasticity computing step, a linear viscosity $C_{lin}$, a nonlinear viscosity $C_{non}$, a linear elastic modulus $K_{lin}$, and a nonlinear elastic modulus $K_{non}$ of the measurement object are computed based on steady-state solutions:

$$x = a \cdot \cos((\beta + 3K_{non}a^2/8\beta)t + C') \quad (2)$$

$$a = 2((G_{lin} - C - C_{lin})/(3C_{non}\beta^2 + G_{non}))^{1/2} \quad (3)$$

$$\beta^2 = 1 + K_{lin} \quad (4)$$

of an equation that holds true with a mechanical model of modeling the oscillator as a spring-mass-dashpot system, a mechanical model of modeling the linear viscosity, the nonlinear viscosity, the linear elasticity, the nonlinear elasticity of the measurement object and the expression (1), where a is an amplitude of the oscillator, C' is an integration constant determined from an initial condition, C is a damping coefficient of the oscillator, K is a spring constant of the oscillator, $C_{lin}$ is the linear viscosity of the measurement object, $C_{non}$ is the nonlinear viscosity of the measurement object, $K_{lin}$ is the linear elasticity of the measurement object, and $K_{non}$ is the nonlinear elasticity of the measurement object.

[Mode 11] A viscoelasticity measurement method according to mode 11 is the structure according to mode 10, wherein in the gain adjustment step, the nonlinear feedback gain $G_{non}$ is increased to decrease the amplitude a so that a term $(\beta+3K_{non}a^2/8\beta)t$ in the expression (2) approximates to $\beta t$, wherein in the physical quantity measurement step, $\beta$, which is an oscillation angular frequency of the oscillator in a state where the term $(\beta+3K_{non}a^2/8\beta)t$ approximates to $\beta t$ is measured, and wherein in the viscoelasticity computing step, the linear elastic modulus $K_{lin}$ is computed based on $\beta$ measured in the physical quantity measurement step and the expression (4).

[Mode 12] A viscoelasticity measurement method according to mode 12 is the structure according to mode 11, wherein in the gain adjustment step, the nonlinear feedback gain $G_{non}$ is changed from the state where the term $(\beta+3K_{non}a^2/8\beta)t$ approximates to $\beta t$, to change the amplitude a of the oscillator and change an oscillation angular frequency $\omega_s$ of the oscillator, wherein in the physical quantity measurement step, the oscillation angular frequency $\omega_s$ of the oscillator and the amplitude a of the oscillator when $G_{non}$ is changed are measured, and wherein in the viscoelasticity computing step, the nonlinear elastic modulus $K_{non}$ is computed based on $$\omega_s = \beta + 3K_{non}a^2/8\beta \quad (5)$$

using the oscillation angular frequency $\omega_s$, the amplitude a, and $\beta$ measured in the physical quantity measurement step.

[Mode 13] A viscoelasticity measurement method according to mode 13 is the structure according to mode 12, wherein in the gain adjustment step, the linear velocity feedback gain $G_{lin}$ is changed, and wherein in the viscoelasticity computing step, the linear viscosity $C_{lin}$ is computed based on a numerator expression $(G_{lin}-C-C_{lin})$ in the expression (3), using: an oscillation limit gain $G_{lin}*$ which is the linear velocity feedback gain when the oscillator changes between an oscillating state and a non-oscillating state; and the damping constant C of the oscillator.

[Mode 14] A viscoelasticity measurement method according to mode 14 is the structure according to mode 13, wherein in the gain adjustment step, the linear velocity feedback gain $G_{lin}$ is increased from a state where the oscillator is self-oscillating, and wherein in the viscoelasticity computing step, the nonlinear viscosity $C_{non}$ is computed based on the expression (3), using $G_{lin}$, C, computed $C_{lin}$, measured $\beta$, and known $G_{non}$.

[Mode 15] To achieve the objects stated above, a viscoelasticity measurement device according to mode 15 is a viscoelasticity measurement device including: an oscillator that is brought into contact with a measurement object; an actuator for causing the oscillator to self-oscillate; an oscillation velocity detection unit for detecting an oscillation velocity of the oscillator; a feedback control unit for, using the oscillation velocity detected by the oscillation velocity detection unit, driving and feedback-controlling the actuator by a feedback control signal defined as $$Fb=(G_{lin}-G_{non} \cdot x^2) \cdot (dx/dt) \quad (6)$$

where Fb is the feedback control signal, $G_{lin}$ is a linear velocity feedback gain which is a positive value, $G_{non}$ is a nonlinear feedback gain, which is a positive value, x is a displacement of the oscillator, and dx/dt is the oscillation velocity of the oscillator; a gain adjustment step for selectively changing one of the linear velocity feedback gain and the nonlinear feedback gain in the feedback control; a physical quantity measurement unit for measuring a physical quantity relating to oscillation of the oscillator when one of the linear velocity feedback gain and the nonlinear feedback gain is changed by the gain adjustment unit; and a viscoelasticity computing unit for computing a linear viscosity, a nonlinear viscosity, a linear elastic modulus, and a nonlinear elastic modulus of the measurement object, based on an equation that holds true with the physical quantity measured by the physical quantity measurement unit, a mechanical model of modelling elasticity and damping of the oscillator, a mechanical model of modelling linear viscosity, nonlinear viscosity, linear elasticity, nonlinear elasticity of the measurement object, and the expression (6).

With such a structure, the oscillation velocity detection unit detects the oscillation velocity dx/dt of the oscillator, and the feedback control unit drives the actuator by the feedback control signal Fb obtained by subtracting, from $G_{lin}(dx/dt)$ obtained by multiplying the detected oscillation velocity dx/dt by the linear velocity feedback gain $G_{lin}$, $G_{non} \cdot x^2 \cdot (dx/dt)$ obtained by multiplying the detected oscillation velocity dx/dt by the nonlinear feedback gain $G_{non}$ and $x^2$. The oscillator in contact with the measurement object is thus controlled. The gain adjustment unit selectively changes one of the linear velocity feedback gain and the nonlinear feedback gain. The physical quantity measurement unit measures the physical quantity relating to the oscillation of the oscillator when one of the linear velocity feedback gain and the nonlinear feedback gain is changed.

The viscoelasticity computing unit then computes the linear viscosity, nonlinear viscosity, linear elastic modulus, and nonlinear elastic modulus of the measurement object based on the equation that holds true with the physical quantity measured by the physical quantity measurement unit, the mechanical model of modelling the elasticity and damping of the oscillator, the mechanical model of modelling the linear viscosity, nonlinear viscosity, linear elasticity, nonlinear elasticity of the measurement object and the expression (6).

As described above, according to modes 1 to 4, the force proportional to the oscillation velocity of the oscillator is applied to the oscillator in contact with the measurement object to cause the oscillator to self-oscillate, and the linear elastic modulus of the measurement object is computed based on the oscillation frequency at the time of self-oscillation. In this way, the linear elastic modulus can be accurately and stably measured even in the case where the measurement object has large damping due to viscous stress. The present invention therefore enables accurate measurement of the elastic modulus of a tenacious viscoelastic body when used in a rheometer and the like. The present invention can also realize, for example, a device for accurately measuring the hardness of a measurement object such as an internal organ.

According to modes 5 to 8, the signal component of the specific frequency is extracted from the displacement signal indicating the displacement of the oscillator, which is output from the displacement sensor. The oscillation velocity of the oscillator is detected based on the signal component. The actuator is feedback-controlled by the feedback control signal obtained by multiplying the oscillation velocity corresponding to the specific frequency by the linear velocity feedback gain, to apply the force proportional to the oscillation velocity to the oscillator and cause the oscillator to self-oscillate. Here, the specific frequency used to extract the signal component is changed, and the feedback gain is changed for the changed specific frequency. Whether or not the oscillator is self-oscillating is detected each time the feedback control using the changed feedback gain is performed, and the feedback gain when the self-oscillation is detected is measured.

This has an advantageous effect of measuring the frequency spectrum of viscoelasticity effective in estimating the internal properties of the viscoelastic body while clearly distinguishing elasticity and viscosity, even in the case where the viscoelastic body has complex viscoelasticity unable to be represented by a simple mechanical model.

According to modes 9 to 15, the oscillator in contact with the measurement object is controlled using nonlinear feedback, while the oscillator is caused to self-oscillate using linear velocity feedback. This enables measurement of not only the linear viscosity and linear elasticity of the material of the measurement object, but also the nonlinear viscosity and nonlinear elasticity of the material of the measurement object. In addition, the time variation of viscosity can be measured in real time.

Moreover, in the case where the viscosity of a liquid is measured, the power spectrum is a line spectrum (i.e., only a natural frequency) because self-oscillation is performed at a natural frequency. The natural frequency can thus be estimated more easily and precisely than in the conventional techniques. Besides, the viscosity can be computed by converting the linear velocity feedback gain that provides a self-oscillation limit.

Furthermore, the amplitude of self-oscillation of the oscillator can be reduced by nonlinear feedback control. Hence, in the case where the measurement object is a fluid, vortex generation is suppressed, and laminar flow is maintained to prevent turbulence.

BRIEF DESCRIPTION OF THE DRAWINGS

FIG. 3 is a schematic block diagram showing an example of a linear elastic modulus measurement device according to Embodiment 1 of the present invention;

FIGS. 5A and 5B are diagrams showing an example of the device structure in the case where the linear elastic modulus measurement device 100 according to Embodiment 1 of the present invention is applied to a thin film material, which is a measurement object;

FIG. 8 is a schematic block diagram showing an example of a viscoelasticity measurement device according to Embodiment 2 of the present invention;

DETAILED DESCRIPTION

Embodiment 1

The following describes Embodiment 1 of a linear elastic modulus measurement method and a linear elastic modulus measurement device according to the present invention, with reference to drawings. FIGS. 1 to 5 are diagrams showing Embodiment 1 of the linear elastic modulus measurement method and the linear elastic modulus measurement device according to the present invention.

(Structure)

Figure 1:
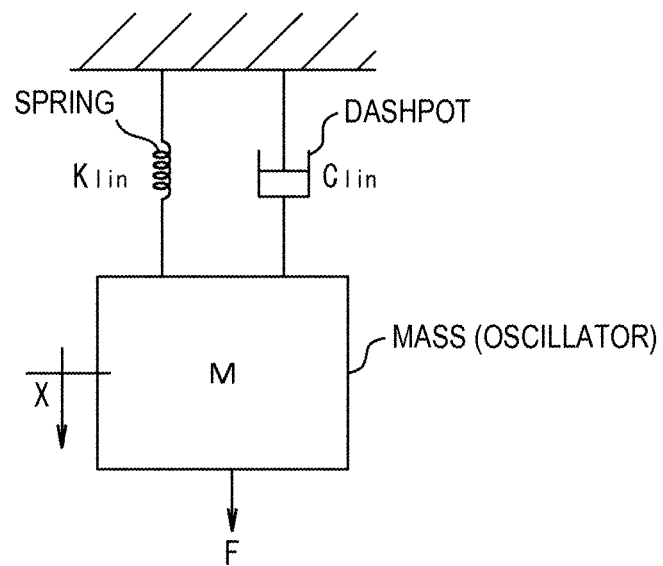
FIG. 1 is a schematic diagram of a mechanical system illustrative of the relations between a linear elastic body, an oscillator, an actuator, and a displacement sensor according to Embodiment 1 of the present invention.

FIG. 1 is a schematic diagram of a mechanical system illustrative of the relations between a linear elastic body, an oscillator, an actuator, and a displacement sensor according to Embodiment 1 of the present invention.

The linear elastic modulus measurement method in this embodiment uses a linear elastic modulus measurement device that includes: an actuator for applying a force to a linear elastic body; a displacement sensor for measuring a displacement; a conversion circuit for differentiating the signal of the displacement sensor to convert it to a velocity output; and a measurement device for measuring an oscillation frequency.

Here, a linear elastic body having both elasticity and viscosity can be replaced by a mechanical system having a spring and a dashpot. Known models of such a mechanical system include, for example, a Maxwell model in which a spring and a dashpot are connected in series and a Kelvin-Voigt model in which a spring and a dashpot are connected in parallel. The Kelvin-Voigt model is used in the example shown in FIG. 1. In the mechanical model in FIG. 1, the linear elastic body which is a measurement object is represented as a structure in which a spring with a linear elastic modulus $K_{lin}$ and a dashpot with viscosity $C_{lin}$ are connected in parallel.

In this embodiment, a force is applied to the linear elastic body via the oscillator having a mass M. This is represented as a mechanical model of a spring-mass-dashpot system in which the oscillator with the mass M is connected to the spring and the dashpot representing the linear elastic body, as shown in FIG. 1. In detail, the oscillator is brought into contact with the linear elastic body. The actuator applies a force F to the oscillator to displace the oscillator (cause the oscillator to self-oscillate), and the displacement sensor detects the displacement of the oscillator. For example, the force F in the shear direction (shear deformation direction) is applied to the linear elastic body via the oscillator, to detect the displacement in the shear direction.

The "contact" mentioned here depends on the physical property and the like of the measurement object. As an example, in the case where the measurement object is a semi-solid, the "contact" indicates that one surface of the oscillator is closely attached to the measurement object. As another example, in the case where the measurement object is a fluid, the "contact" indicates that the oscillator such as a cantilever is inserted into the fluid.

In such a structure, when the force F is applied to the linear elastic body (the oscillator in a precise sense), the displacement occurs according to an equation of motion shown in the following expression (7).

$$M(d^2x/dt^2)+C_{lin}(dx/dt)+K_{lin}x=F \quad (7).$$

In the expression (7), M is the mass of the oscillator, $C_{lin}$ is the proportionality coefficient of the viscous term, $K_{lin}$ is the linear elastic modulus, and x is the displacement of the linear elastic body (equivalent to the displacement of the oscillator). In this embodiment, the force F (hereafter denoted by Fv) proportional to the motion velocity of the linear elastic body is applied to the linear elastic body. In such a case, the equation of motion is written as the following expression (8).

$$M(d^2x/dt^2)+C_{lin}(dx/dt)+K_{lin}x=G_{lin}(dx/dt) \quad (8).$$

In the expression (8), $G_{lin}$ is the proportionality coefficient of the input force and the velocity, and is hereafter referred to as "linear velocity feedback gain". Moving the right side of the expression (8) to the left side yields the following expression (9).

$$M(d^2x/dt^2)+(C_{lin}-G_{lin})(dx/dt)+K_{lin}x=0 \quad (9).$$

When the linear velocity feedback gain $G_{lin}$ exceeds the proportionality constant $C_{lin}$ of the viscous term, a negative viscous term is generated, and the linear elastic body self-oscillates. The oscillation angular frequency at the time can be given by the following expression (10).

$$\omega_s=(K_{lin}/M)^{1/2} \quad (10).$$

In the expression (10), $\omega_s$ is the angular frequency of self-induced oscillation (self-oscillation). From the expression (10), if the oscillation angular frequency $\omega_s$ of self-oscillation can be measured, then the linear elastic modulus $K_{lin}$ can be computed using the following expression (11) obtained by modifying the expression (10).

$$K_{lin}=\omega_s^2 \times M \quad (11).$$

Figure 2A:
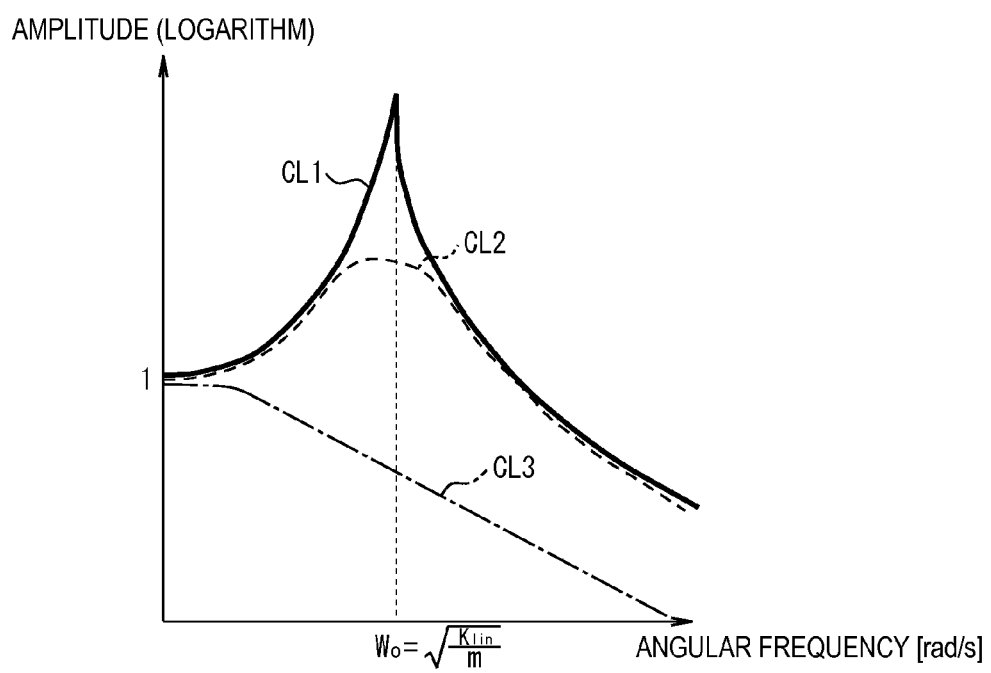
FIG. 2A is a diagram showing an example of frequency response curves of three types of linear elastic bodies different in viscous stress in the case where a conventional measurement method is used.
Figure 2B:
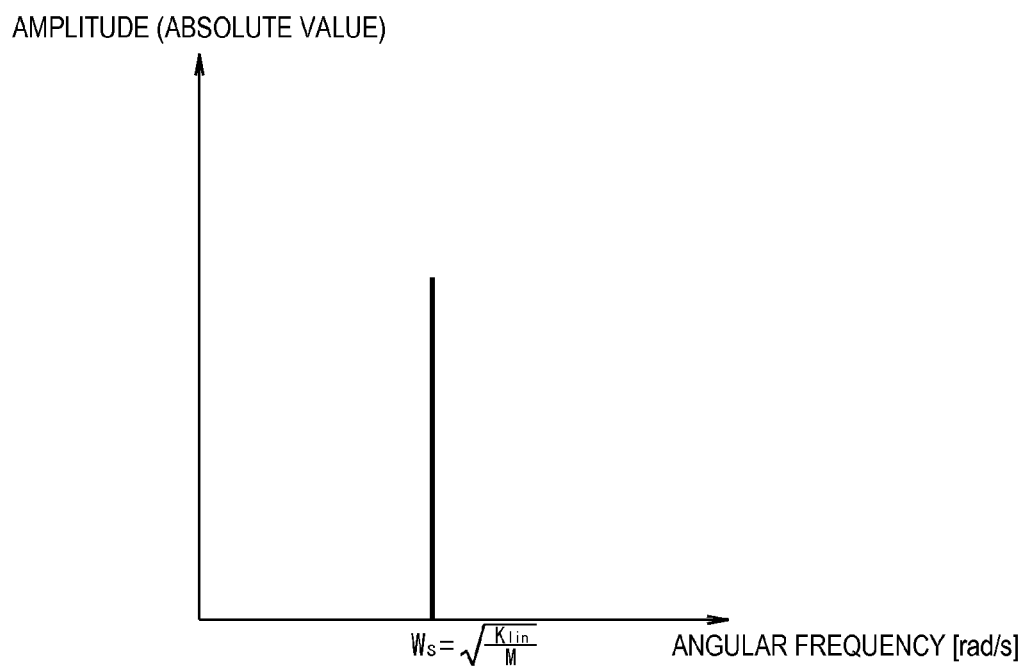
FIG. 2B is a diagram showing an example of a frequency response curve in the case where a measurement method according to the present invention is used.

The following describes the problem with the conventional measurement method that uses the resonance method, with reference to FIGS. 2A and 2B. FIG. 2A is a diagram showing an example of frequency response curves of three types of linear elastic bodies different in viscous stress in the case where the conventional measurement method is used, and FIG. 2B is a diagram showing an example of a frequency response curve in the case where the measurement method according to the present invention is used. In each, the vertical axis represents the amplitude of the linear elastic body, and the horizontal axis represents the oscillation angular frequency of the linear elastic body.

When a sinusoidal forced oscillation force $F=Fo \cdot \sin \omega_t$ (Fo is the amplitude of the oscillation force) is applied to the linear elastic body as in the conventional method, the linear elastic body oscillates in a sinusoidal wave as $x=A \cdot \sin(\omega_t+\varphi)$. Here, A is the amplitude of the displacement, and $\varphi$ is the phase. The amplitude A changes as shown in FIG. 2A, according to the angular frequency of the forced oscillation force F. The frequency response curve differs depending on the magnitude of viscous stress. In the case where the viscous stress is small, the Q factor is high, and the frequency response curve has a sharp peak as indicated by curve CL1 in FIG. 2A. The angular frequency $\omega_o$ of the peak can be approximated by $\omega_o=(K_{lin}/M)^{1/2}$, and the linear elastic modulus $K_{lin}$ can be computed from this expression. In the case where the viscous stress is large, however, the Q factor is low, and the approximation no longer applies. Besides, the peak is gentle as indicated by curve CL2 in FIG. 2A, making it difficult to identify the peak position. In the case where the viscous stress is larger and the Q factor is lower, the viscous stress exceeds an over-damping condition, and no peak appears as indicated by curve CL3 in FIG. 2A.

In the linear elastic modulus measurement method according to the present invention, on the other hand, the force F applied to the linear elastic body is the force Fv proportional to the velocity of the linear elastic body. Accordingly, the linear elastic body self-oscillates, and its angular frequency is $\omega_s=(K_{lin}/M)^{1/2}$ as shown in the expression (10). A frequency response curve representing this has a sharp peak only at $\omega_s$, as shown in FIG. 2B. This curve does not depend on the viscous stress. Hence, the linear elastic modulus $K_{lin}$ can be measured from the angular frequency $\omega_s$ of self-oscillation, regardless of the magnitude of viscous stress.

The following describes the schematic structure of the linear elastic modulus measurement device according to this embodiment, with reference to FIG. 3. FIG. 3 is a schematic block diagram showing an example of the linear elastic modulus measurement device according to this embodiment.

As shown in FIG. 3, a linear elastic modulus measurement device 100 according to this embodiment includes an oscillator 1, a displacement sensor 2, a displacement detector 3, an oscillation velocity computing unit 4, a gain adjustment unit 5a, an amplifier 5b, an actuator 6, a driver 7, a frequency detection unit 8, a self-oscillation detection unit 9, and a computing unit 10.

The oscillator 1 is a structure having the mass M and made of a semiconductor material or the like. The material, shape, and the like of the oscillator 1 differ depending on the physical property and the like of the linear elastic body as the measurement object. To measure the linear elastic modulus $K_{lin}$ of the linear elastic body, the oscillator 1 is brought into contact with the linear elastic body. In the case where the linear elastic body is a thin film material such as a coating agent, the oscillator 1 is a structure whose cross section is rectangular (e.g. a cube) as an example, and one surface of the oscillator 1 is closely attached to the thin film. In the case where the linear elastic body is a fluid, the oscillator 1 is shaped like a cantilever as an example, and its probe is inserted into the fluid.

The displacement sensor 2 is a sensor for detecting the displacement of the oscillator 1, and supplies the sensor output to the displacement detector 3.

The displacement detector 3 detects the displacement x of the oscillator 1 based on the sensor output from the displacement sensor 2, and supplies the detected displacement x to the oscillation velocity computing unit 4, the frequency detection unit 8, and the self-oscillation detection unit 9.

Examples of the displacement sensor 2 or the combination of the displacement sensor 2 and the displacement detector 3 include an electrostatic capacitance displacement sensor, an encoder, an optical displacement meter, and a strain gauge.

The oscillation velocity computing unit 4 includes a differentiator. The oscillation velocity computing unit 4 differentiates the displacement x from the displacement detector 3 by the differentiator to compute the oscillation velocity dx/dt of the oscillator 1, and supplies computed dx/dt to the amplifier 5b.

The gain adjustment unit 5a sets an initial value of the linear velocity feedback gain Glin of the amplifier 5b, and changes the gain $G_{lin}$ of the amplifier 5b based on a signal (described later) from the self-oscillation detection unit 9 indicating that the oscillator 1 is detected not self-oscillating. In detail, each time the gain adjustment unit 5a receives a signal from the self-oscillation detection unit 9 indicating that the oscillator 1 is detected not self-oscillating, the gain adjustment unit 5a increases (or decreases) the gain by preset Δg. The gain adjustment is repeatedly performed until the self-oscillation detection unit 9 detects that the oscillator 1 is self-oscillating.

The amplifier 5b includes a variable amplifier. The amplifier 5b multiplies the linear velocity feedback gain $G_{lin}$ set by the gain adjustment unit 5a and the oscillation velocity dx/dt supplied from the oscillation velocity computing unit 4, and supplies computed $G_{lin} \cdot dx/dt$ to the driver 7 as a feedback control signal Fs.

The actuator 6 applies, to the oscillator 1, the force Fv proportional to the motion velocity of the oscillator 1, based on a drive signal supplied from the driver 7. Examples of the actuator 6 include a piezo element, a voice coil motor, and an electrostatic actuator.

The driver 7 generates, based on the feedback control signal Fs supplied from the amplifier 5b, the drive signal for driving the actuator 6 to apply the force Fv proportional to the motion velocity of the oscillator 1 to the oscillator 1, and supplies the generated drive signal to the actuator 6. For example, the driver 7 supplies the drive signal obtained by amplifying the feedback control signal Fs to the actuator 6.

The frequency detection unit 8 detects the frequency of the oscillation waveform formed by the displacement x, based on the displacement x of the oscillator 1 supplied from the displacement detector 3. The frequency detection unit 8 supplies the detected frequency $f_s$ to the computing unit 10.

Examples of the frequency detection unit 8 include a frequency counter, Fast-Fourier Transform (FFT) analyzer, and a spectrum analyzer.

The self-oscillation detection unit 9 detects whether or not the oscillator 1 is self-oscillating, based on the oscillation displacement x (or the oscillation velocity dx/dt, or the frequency spectrum of the oscillation amplitude). In the case of detecting that the oscillator 1 is self-oscillating, the self-oscillation detection unit 9 supplies a signal indicating the detection to the gain adjustment unit 5a and the computing unit 10.

In the case of detecting that the oscillator 1 is not self-oscillating, the self-oscillation detection unit 9 supplies a signal indicating the detection to the gain adjustment unit 5a.

The computing unit 10 computes the linear elastic modulus $K_{lin}$ of the measurement object according to the expression (11) based on the frequency $f_s$ at the time of detection of self-oscillation (hereafter referred to as "oscillation frequency $f_s$") and the preset mass M of the oscillator 1, in response to the signal indicating that the oscillator 1 is detected self-oscillating. In detail, the computing unit 10 multiplies the oscillation frequency $f_s$ by $2\pi$, to compute the oscillation angular frequency $\omega_s$. The computing unit 10 then squares the oscillation angular frequency $\omega_s$ to obtain $\omega_s^2$, and multiplies $\omega_s^2$ by the mass M to compute the linear elastic modulus $K_{lin}$.

When the computing unit 10 computes the linear elastic modulus $K_{lin}$, the gain adjustment unit 5a adjusts the linear velocity feedback gain $G_{lin}$ at the time of detection of self-oscillation to $G_{lin}+\Delta g2$ ($\Delta g2$ is a preset increment). Further, the amplifier 5b keeps the feedback control signal $F_s$ supplied to the driver 7, at $(G_{lin}+\Delta g2) \cdot dx/dt$. The frequency detection unit 8 detects the frequency $f_s$ of the oscillation waveform formed by the oscillation displacement x at the time. The computing unit 10 may then compute the linear elastic modulus $K_{lin}$ using this frequency $f_s$.

The linear elastic modulus measurement device 100 in this embodiment includes a computer system for realizing each of the above-mentioned functions by software or for controlling hardware for realizing each of the above-mentioned functions, though not shown.

In detail, the linear elastic modulus measurement device 100 includes: a central processing unit (CPU) performing various control and operations; a random access memory (RAM) functioning as a work memory; a read only memory (ROM) storing dedicated programs for realizing each of the above-mentioned functions, data necessary for executing the programs, and the like; and a data transmission bus for transmitting data to each component.

(Linear Elastic Modulus Measurement Process)

Figure 4:
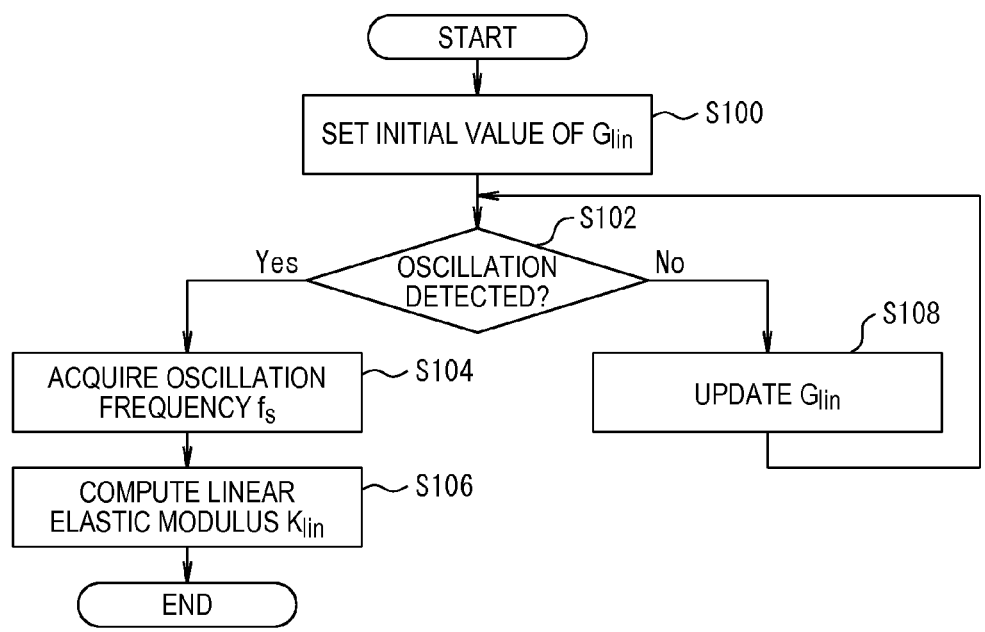
FIG. 4 is a flowchart showing an example of a procedure of a linear elastic modulus measurement process.

The following describes a procedure of a linear elastic modulus measurement process executed in the linear elastic modulus measurement device 100, with reference to FIG. 4. FIG. 4 is a flowchart showing an example of the procedure of the linear elastic modulus measurement process.

As shown in FIG. 4, the procedure first proceeds to step S100, and the gain adjustment unit 5a sets the linear velocity feedback gain $G_{lin}$ of the amplifier 5b to the initial value. The procedure then proceeds to step S102. The initial value may be any value such as 0.

In step S102, the self-oscillation detection unit 9 determines whether or not the oscillator 1 is oscillating (self-oscillating). In the case of determining that the oscillator 1 is oscillating (Yes), the self-oscillation detection unit 9 supplies a signal indicating that the oscillator 1 is detected oscillating, to the computing unit 10. The procedure then proceeds to step S104. In the case of determining that the oscillator 1 is not oscillating (No), the self-oscillation detection unit 9 supplies a signal indicating that the oscillator 1 is detected not oscillating, to the gain adjustment unit 5a. The procedure then proceeds to step S108.

Whether or not the oscillator 1 is oscillating is determined as follows. For example, the self-oscillation detection unit 9 may determine that the oscillator 1 is oscillating, in the case where the oscillation displacement x or the oscillation velocity dx/dt changes by a preset threshold or more. Alternatively, the self-oscillation detection unit 9 may compute the frequency spectrum of the oscillation amplitude of the oscillator 1 by, for example, performing a FFT on the oscillation displacement data made up of the oscillation displacement x and, in the case where a spectrum of a single oscillation frequency is generated, determine that the oscillator 1 is oscillating.

In the case where the procedure proceeds to step S104, the computing unit 10 acquires the oscillation frequency fs from the frequency detection unit 8, in response to the signal from the self-oscillation detection unit 9 indicating that the oscillator 1 is detected oscillating. The procedure then proceeds to step S106.

In step S106, the computing unit 10 computes the oscillation angular frequency $\omega_s$ from the oscillation frequency $f_s$ acquired in step S104, and squares the oscillation angular frequency $\omega_s$ to obtain $\omega_s^2$. The computing unit 10 multiplies $\omega_s^2$ by the mass M of the oscillator 1, to compute the linear elastic modulus $K_{lin}$. This completes the process.

In the case where no oscillation (self-oscillation) is detected in step S102 and the procedure proceeds to step S108, the gain adjustment unit 5a increases the current linear velocity feedback gain $G_{lin}$ set in the amplifier 5b by preset Δg, in response to the signal from the self-oscillation detection unit 9 indicating that the oscillator 1 is detected not oscillating. The procedure then proceeds to step S102. The linear velocity feedback gain $G_{lin}$ may be changed successively, or changed by a preset change amount.

Thus, steps S102 and S108 are repeatedly performed to increase the linear velocity feedback gain $G_{lin}$, until the oscillator 1 is determined as oscillating in step S102. When the oscillator 1 oscillates, the procedure proceeds from step S102 to step S104. The oscillation frequency of the oscillator 1 at the time is acquired as the oscillation frequency $f_s$.

Here, Δg is set to such a relatively small value that allows the oscillation frequency $f_s$ to be detected from the oscillation displacement x of the oscillator 1, when the linear velocity feedback gain $G_{lin}$ is kept at "$G_{lin}$+Δg". When Δg is larger, the linear velocity feedback gain $G_{lin}$ is larger, causing the oscillation amplitude of the oscillator 1 to increase. As a result, the oscillation frequency $f_s$ of the oscillator 1 deviates from the linear natural frequency, and the oscillation frequency $f_s$ easily varies with a slight change in oscillation amplitude. This increases the detection error of $\omega_s$ in the expression (11), and leads to lower computation accuracy of the linear elastic modulus $K_{lin}$. Accordingly, Δg is preferably as small as possible.

(Operation)

The following describes the operation of the linear elastic modulus measurement device 100 in this embodiment, with reference to FIG. 5.

FIG. 5 is a diagram showing an example of the device structure of the linear elastic modulus measurement device 100 in the case where the linear elastic modulus measurement method in this embodiment is applied to a thin film material, which is the measurement object.

As shown in FIG. 5A, the linear elastic body as the measurement object is a thin film material bonded onto a fixed substrate, and the oscillator 1 with the mass M is closely attached to the thin film material. The oscillator 1 is formed by providing a cubic structure 1b with the mass M at one end of a needle-like rod body 1a, and the lower end surface of the structure 1b is closely attached to the thin film material. In the example in FIG. 5, a voice coil motor is used as the actuator 6 for causing the oscillator 1 to self-oscillate. The voice coil motor can apply the force Fv in the shear deformation direction of the thin film material.

For example, in the case where the force Fv is applied in the direction shown in FIG. 5A, the displacement of the oscillator 1 by the force Fv causes the thin film material to undergo shear deformation in the displacement direction shown in FIG. 5B.

The use of the voice coil motor as the actuator 6 enables contactless application of the force Fv to the oscillator 1. An electrostatic capacitance displacement meter (corresponding to the displacement sensor 2 and the displacement detector 3) detects the displacement x of the oscillator 1, and supplies the detected displacement signal (the displacement x) to the oscillation velocity computing unit 4 connected to the electrostatic capacitance displacement meter. The oscillation velocity computing unit 4 computes the oscillation velocity dx/dt of the oscillator 1, and supplies the computed oscillation velocity dx/dt to the amplifier 5b. The amplifier 5b multiplies the oscillation velocity dx/dt by the linear velocity feedback gain $G_{lin}$, and supplies computed $G_{lin}\cdot dx/dt$ to a control circuit (corresponding to the driver 7) of the voice coil motor as the feedback control signal $F_s$. The electrostatic capacitance displacement meter also supplies the displacement signal to a frequency counter (corresponding to the frequency detection unit 8) connected to the electrostatic capacitance displacement meter, and the frequency counter detects the oscillation frequency fs of the oscillator 1.

The following describes the operation of the linear elastic modulus measurement device 100 having the device structure shown in FIG. 5A.

Before the measurement, the mass M of the oscillator 1 is precisely measured, and the measured mass M is stored in a memory (e.g. the RAM). Regarding the mass M, the mass of the rod body 1a may be ignored in the case where the mass of the structure 1b provided at one end of the rod body 1a is sufficiently larger than the mass of the rod body 1a. By taking into account the mass of the rod body 1a, however, it is possible to measure the linear elastic modulus more accurately. The mass M stored in the memory is used by the computing unit 10 when self-oscillation is detected.

Next, the gain adjustment unit 5a sets the linear velocity feedback gain $G_{lin}$ of the amplifier 5b to the initial value (a small value) (step S100). The power switch of each component is then turned on. This starts the measurement.

In an initial stage when the measurement starts, the oscillator 1 is not displaced, so that the displacement x detected by the electrostatic capacitance displacement meter is 0, and the oscillation velocity dx/dt is 0. Actually, however, the displacement x is not 0 and has some value, due to noise in the surrounding environment and the like. The electrostatic capacitance displacement meter detects this displacement x, and the oscillation velocity computing unit 4 computes the oscillation velocity dx/dt from the displacement x. The oscillation velocity computing unit 4 supplies the oscillation velocity dx/dt to the amplifier 5b. The amplifier 5b multiplies the set linear velocity feedback gain $G_{lin}$ and dx/dt, and supplies the multiplication result $G_{lin}\cdot dx/dt$ to the control circuit of the voice coil motor as the feedback control signal $F_s$.

In the case where, in the initial stage of self-oscillation, the displacement of the oscillator 1 merely caused by noise in the surrounding environment and the like is less than the detection lower limit of the electrostatic capacitance displacement meter, oscillation of a given frequency is applied preliminarily. In detail, the oscillator 1 is caused to oscillate at a given constant frequency.

The control circuit generates the drive signal for the voice coil motor for applying the force Fv proportional to the oscillation velocity dx/dt of the oscillator 1 to the oscillator 1, based on $G_{lin}\cdot dx/dt$ received from the amplifier 5b. The control circuit supplies the generated drive signal to the voice coil motor. The voice coil motor is driven by the drive signal, and applies the force Fv to the oscillator 1. A feedback loop is thus formed, and the voice coil motor applies the force Fv proportional to the oscillation velocity of the oscillator 1. Meanwhile, the displacement signal from the electrostatic capacitance displacement meter is supplied to the frequency counter as needed, and the frequency counter detects the oscillation frequency of the oscillator 1.

The self-oscillation detection unit 9 compares the oscillation displacement x of the oscillator 1 with a preset threshold, based on the displacement signal supplied from the electrostatic capacitance displacement meter. The self-oscillation detection unit 9 determines whether or not the oscillator 1 is oscillating, based on the comparison result (step S102). In the case where the displacement x is less than the threshold and the oscillator 1 is determined as not oscillating (step S102: No), the self-oscillation detection unit 9 supplies a signal indicating that the oscillator 1 is detected not oscillating, to the gain adjustment unit 5a. The gain adjustment unit 5a accordingly increases the linear velocity feedback gain Glin of the amplifier 5b by Δg (step S108). This increase process is performed each time the gain adjustment unit 5a receives a signal indicating that the oscillator 1 is detected not oscillating.

When the linear velocity feedback gain $G_{lin}$ is gradually increased in this way, the linear velocity feedback gain $G_{lin}$ eventually exceeds the proportionality constant $C_{lin}$ of the viscous term shown in the expression (9), and self-oscillation occurs. That is, the self-oscillation detection unit 9 detects that the displacement x is greater than or equal to the threshold, and determines the oscillator 1 as self-oscillating (step S102: Yes). The self-oscillation detection unit 9 supplies a signal indicating that the oscillator 1 is detected self-oscillating, to the computing unit 10.

Upon receiving the signal indicating that the oscillator 1 is detected self-oscillating, the computing unit 10 acquires the oscillation frequency fs from the frequency counter (step S104). The computing unit 10 computes the linear elastic modulus $K_{lin}$ of the thin film material according to the expression (11), from the acquired oscillation frequency $f_s$ and the mass M stored in the memory (step S106). In detail, the computing unit 10 multiplies the measurement value fs of the frequency counter at the time of self-oscillation by 2π, and multiplies its square by the mass M, to determine the linear elastic modulus $K_{lin}$ of the thin film material.

As described above, the linear elastic modulus measurement method and the linear elastic modulus measurement device 100 in this embodiment enable the following. In a state where the oscillator 1 with the mass M is in contact with the linear elastic body, the force Fv proportional to the oscillation velocity of the oscillator 1 is applied to the oscillator 1, to cause the oscillator 1 to self-oscillate. The linear elastic modulus $K_{lin}$ of the linear elastic body is then computed according to the expression (11), based on the frequency $f_s$ at the time of self-oscillation of the oscillator 1 and the mass M of the oscillator 1.

In this way, the linear elastic modulus can be accurately and stably measured even in the case where the measurement object has large damping due to viscous stress. The present invention therefore enables accurate measurement of the elastic modulus of a tenacious viscoelastic body, when used in a rheometer and the like. The present invention can also realize, for example, a device for accurately measuring the hardness of a measurement object such as an internal organ.

In the case where the displacement x of the oscillator 1 is less than the detection lower limit of the displacement sensor in the initial stage of self-oscillation, preliminary oscillation is applied to the oscillator 1. This prevents a situation where the measurement cannot be performed because no displacement is detected.

In the foregoing embodiment, the amplifier 5b and the driver 7 constitute a feedback control unit, the oscillation velocity computing unit 4 constitutes an oscillation velocity detection unit, and the computing unit 10 constitutes a linear elastic modulus computing unit.

In the foregoing embodiment, step S102 corresponds to a step of detecting whether or not the oscillator is self-oscillating, and step S108 corresponds to a step of changing the linear velocity feedback gain.

In the foregoing embodiment, steps S104 to S106 correspond to a step of computing a linear elastic modulus.

Embodiment 2

The following describes Embodiment 2 of a viscoelasticity measurement method and a viscoelasticity measurement device according to the present invention, with reference to drawings. FIGS. 6 to 10 are diagrams showing Embodiment 2 of the viscoelasticity measurement method and the viscoelasticity measurement device according to the present invention.

(Structure)

Figure 6A:
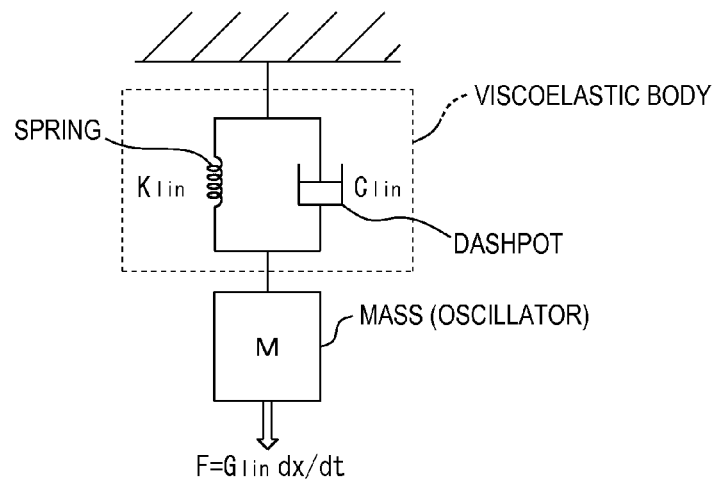
FIG. 6A is a schematic diagram of a mechanical system illustrative of the relations between a viscoelastic body, an oscillator, an actuator, and a displacement sensor according to Embodiment 2 of the present invention.
Figure 6B:
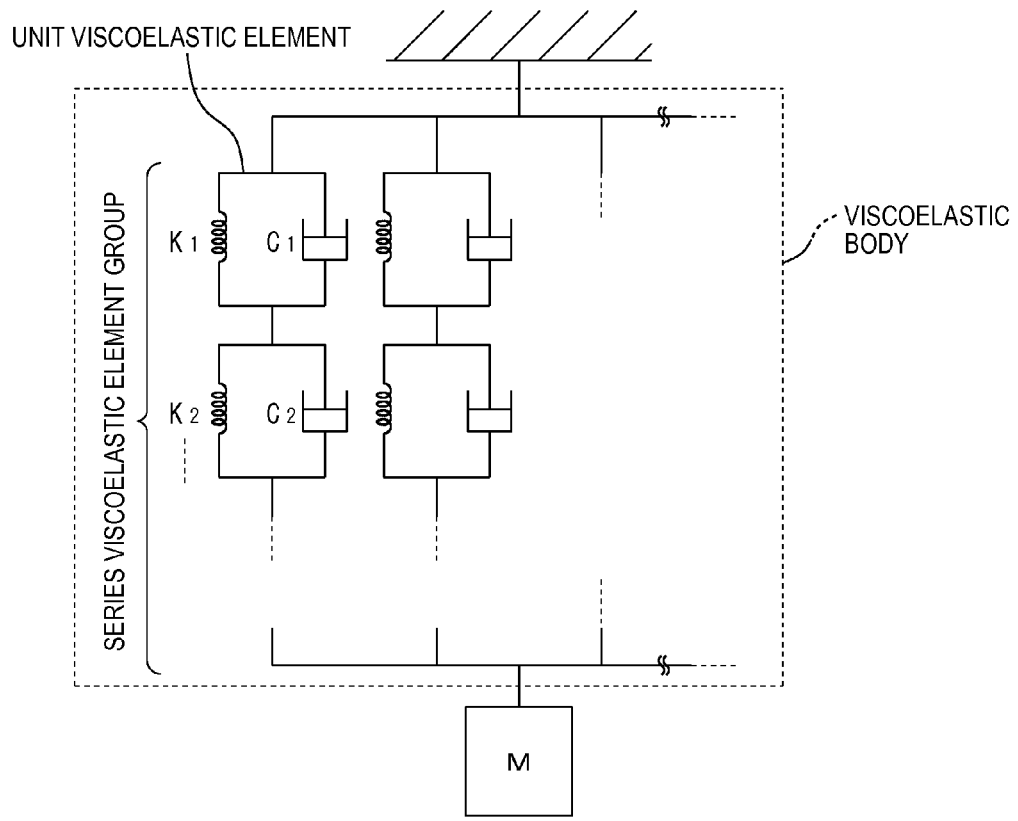
FIG. 6B is a schematic diagram showing an exemplary structure of a mechanical system of a viscoelastic body having a complex molecular and microscopic structure.

FIG. 6A is a schematic diagram of a mechanical system illustrative of the relations between a viscoelastic body, an oscillator, an actuator, and a displacement sensor according to Embodiment 2 of the present invention, and FIG. 6B is a schematic diagram showing an exemplary structure of a mechanical system of a viscoelastic body having a complex molecular and microscopic structure.

The viscoelasticity measurement method in this embodiment uses a viscoelasticity measurement device that includes: an oscillator brought into contact with a viscoelastic body; an actuator for applying deformation to the viscoelastic body via the oscillator; a displacement sensor for measuring the displacement of the viscoelastic body (oscillator); a bandpass filter for extracting a signal component of a specific frequency from a displacement signal output from the displacement sensor; means for changing the passing frequency band (specific frequency band) of the bandpass filter; a conversion circuit for differentiating the specific frequency component of the displacement signal to obtain the oscillation velocity, and for multiplying the oscillation velocity by a feedback gain to convert it to a force output; means for changing the feedback gain in each specific frequency band, and for detecting whether or not self-oscillation occurs in each specific frequency band; and means for measuring the feedback gain at the time of detection of self-oscillation.

Here, a viscoelastic body having both elasticity and viscosity can be replaced by a mechanical system having a spring and a dashpot. Known models of such a mechanical system include, for example, a Maxwell model in which a spring and a dashpot are connected in series and a Kelvin-Voigt model in which a spring and a dashpot are connected in parallel. The Kelvin-Voigt model is used in the example shown in FIG. 6A, which is a diagram necessary to describe the theoretical background of this embodiment. The mechanical model in FIG. 6A is a mechanical model that can be represented by a simple mechanical system where the elasticity and viscosity of the viscoelastic body are each composed of only one element. In detail, the viscoelastic body which is a measurement object is represented as a structure in which a spring with one linear elastic modulus $K_{lin}$ and a dashpot with one linear viscosity $C_{lin}$ are connected in parallel.

In the case where a deformation force is applied to the viscoelastic body via the oscillator having a mass M, the structure can be represented as a mechanical model of a spring-mass-dashpot system in which the oscillator with the mass M is connected to the spring and the dashpot representing the viscoelastic body, as shown in FIG. 6A. In detail, the oscillator is brought into contact with the viscoelastic body. The actuator applies a force F to the oscillator to displace the oscillator (cause the oscillator to self-oscillate), and the displacement sensor detects the displacement of the oscillator as the displacement of the viscoelastic body. For example, the force F in the shear direction (shear deformation direction) is applied to the viscoelastic body via the oscillator to detect the displacement in the shear direction.

The "contact" mentioned here depends on the physical property and the like of the viscoelastic body. As an example, in the case where the viscoelastic body is a semisolid, the "contact" indicates that one surface of the oscillator is closely attached to the measurement object. As another example, in the case where the viscoelastic body is a fluid, the "contact" indicates that the oscillator such as a cantilever is inserted into the fluid.

In such a structure, when the force F is applied to the viscoelastic body (the oscillator in a precise sense), the displacement occurs according to an equation of motion shown in the following expression (12).

$$M(d^2x/dt^2)+C_{lin}(dx/dt)+K_{lin}x=F \quad (12)$$

In the expression (12), M is the mass of the oscillator, $C_{lin}$ is the proportionality coefficient (linear viscosity) of the viscous term, $K_{lin}$ is the linear elastic modulus, and x is the displacement of the viscoelastic body (equivalent to the displacement of the oscillator). In the case where the force F (hereafter denoted by Fv) proportional to the motion velocity of the viscoelastic body is applied to the viscoelastic body, the equation of motion is written as the following expression (13).

$$M(d^2x/dt^2)+C_{lin}(dx/dt)+K_{lin}x=G_{lin}(dx/dt) \quad (13)$$

In the expression (13), Glin is the proportionality coefficient of the input force and the velocity, and is hereafter referred to as "linear velocity feedback gain". Moving the right side of the expression (13) to the left side yields the following expression (14).

$$M(d^2x/dt^2)+(C_{lin}-G_{lin})(dx/dt)+K_{lin}x=0 \quad (14)$$

When the linear velocity feedback gain $G_{lin}$ exceeds the proportionality constant $C_{lin}$ of the viscous term, a negative viscous term is generated, and the viscoelastic body self-oscillates. The oscillation angular frequency at the time can be given by the following expression (15).

$$\omega_s=(K_{lin}/M)^{1/2} \quad (15)$$

In the expression (15), $\omega_s$ is the angular frequency of self-induced oscillation (self-oscillation). From the expression (15), if the oscillation angular frequency $\omega_s$ of self-oscillation can be measured, then the linear elastic modulus $K_{lin}$ can be computed using the following expression (16) obtained by modifying the expression (15).

$$K_{lin}=\omega_s^2 \times M \quad (16)$$

Thus, in the case where the viscoelastic body can be represented by a simple mechanical model, self-oscillation can be theoretically described, with it being possible to compute the elastic modulus and the viscosity.

However, the viscoelasticity of a viscoelastic body having a complex molecular and microscopic structure, such as molten plastic or rubber, may be unable to be modeled by a simple mechanical model as shown in FIG. 6A. In such a case, it is extremely difficult to determine the accurate internal mechanical structure of the viscoelastic body.

The present inventors assume that the internal mechanical structure of a viscoelastic body having a complex molecular and microscopic structure is a mixture of a plurality of viscoelastic elements (for example, viscoelastic elements (hereafter referred to as "unit viscoelastic elements") of the structure shown in FIG. 6A different in elastic modulus and viscosity, and represent the viscoelastic body having the complex molecular and microscopic structure by a model shown in FIG. 6B.

In detail, the viscoelastic body having the complex molecular and microscopic structure is represented by a model in which a plurality of unit viscoelastic elements different in elastic modulus and viscosity are connected in series, and series viscoelastic element groups each of which is made up of the series-connected unit viscoelastic elements are connected in parallel, with the mass M (oscillator) being connected to the parallel-connected series viscoelastic element groups, as shown in FIG. 6B.

Figure 7A:
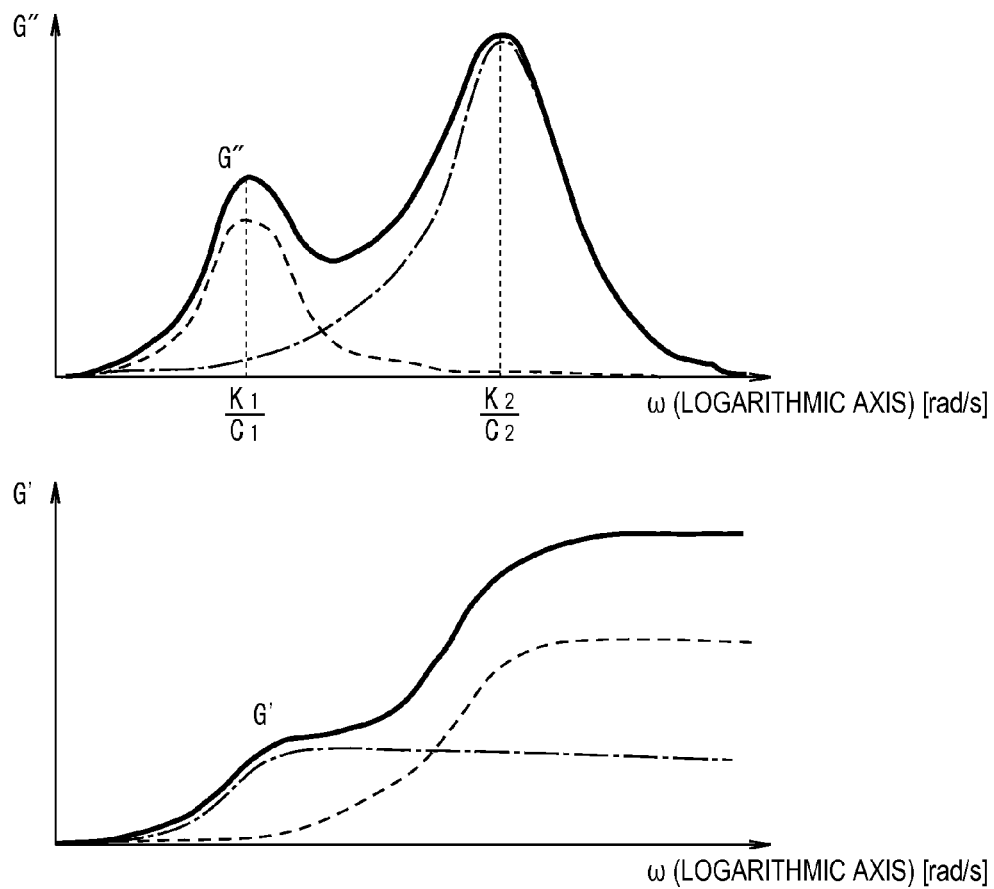
FIG. 7A is a diagram showing an example of frequency response curves of a dynamic elastic modulus and a loss elastic modulus corresponding to each of a plurality of relaxation times.
Figure 7B:
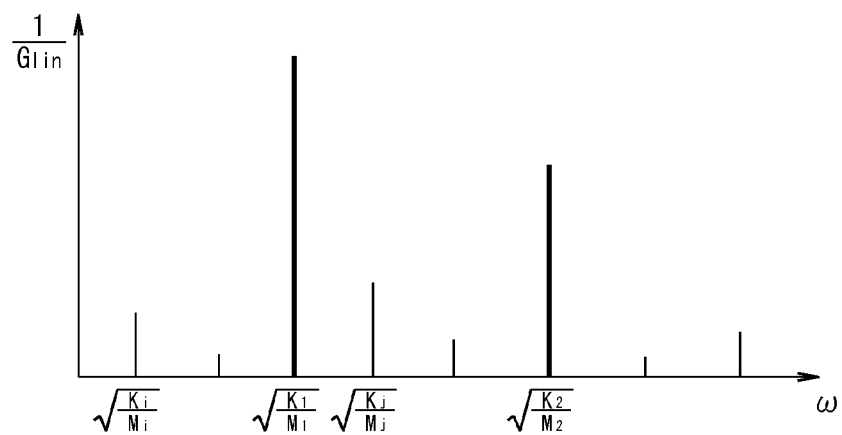
FIG. 7B is a diagram showing an example of viscoelastic spectra obtained by a viscoelasticity measurement method according to Embodiment 2 of the present invention.

The following describes the problem with the conventional measurement method used in rheometers, with reference to FIGS. 7A and 7B. FIG. 7A is a diagram showing an example of frequency response curves of a dynamic elastic modulus and a loss elastic modulus corresponding to each of a plurality of relaxation times, and FIG. 7B is a diagram showing an example of viscoelastic spectra obtained by the viscoelasticity measurement method according to this embodiment.

In the conventional method, it is assumed that a complex viscoelastic body that needs to be represented by the model in FIG. 6B has a plurality of relaxation times, and the curve of each of the dynamic elastic modulus (G') and the loss elastic modulus (G") is formed by superimposing the waveforms corresponding to the plurality of relaxation times, as shown in FIG. 7A. Based on this assumption, inflection points or peaks are read from the measurement results of the dynamic elastic modulus and the loss elastic modulus to estimate the microscopic mechanical structure of the viscoelastic body.

However, the dynamic elastic modulus has a waveform with gentle peaks as shown in the lower diagram in FIG. 7A, and the loss elastic modulus has a gentle monotonically increasing curve with an upper limit as shown in the upper diagram in FIG. 7A. Therefore, despite the difference in relaxation time and elastic modulus, the superimposed waveforms merely form a gentle curve with little characteristics. Particularly in the case where the relaxation times are close to each other or the elastic moduli are small, it is difficult to clearly distinguish the curve for each relaxation time.

In the viscoelastic measurement method according to the present invention, on the other hand, it is assumed that the combination of each of the plurality of unit viscoelastic elements and the added mass in the model in FIG. 6B induces self-oscillation at a different frequency. Hence, self-oscillation is checked for each frequency, and the ratio of the viscosity, the elastic modulus, and the added mass corresponding to one of the combinations of the added mass and the unit viscoelastic elements is clearly specified from the checked frequency and the linear velocity feedback gain $G_{lin}$.

As shown in FIG. 7B, each spectrum where the vertical axis represents the inverse ($1/G_{lin}$) of the linear velocity feedback gain and the horizontal axis represents the angular frequency (ω) appears as a sharp peak corresponding to a different one of the combinations of the added mass and the unit viscoelastic elements in the model in FIG. 6B, and can be clearly distinguished from each other. Consider the case where measurement is performed for displacement signal components corresponding to n specific frequencies $fp_i$ where n is a natural number greater than or equal to 2 and i=1, 2, 3, . . . , (n−1), n. From the angular frequency $ωp_i$ of the peak corresponding to each of the n displacement signal components, the square root $((K_i/M_i)^{1/2})$ of the ratio of the linear elastic modulus $K_i$ and the added mass $M_i$ corresponding to the angular frequency $ωp_i$ can be determined. The magnitude ($1/G_i$) of the inverse of the linear viscosity corresponding to the angular frequency $ωp_i$ can be determined from the peak height. Thus, according to the present invention, even with a complex viscoelastic body that needs to be represented by the model in FIG. 6B, a sharp peak corresponding to a mechanical component can be obtained and a viscoelastic spectrum much clearer than that in the conventional method can be measured.

The following describes the schematic structure of the viscoelasticity measurement device according to this embodiment, with reference to FIG. 8. FIG. 8 is a schematic block diagram showing an example of the viscoelasticity measurement device according to this embodiment.

As shown in FIG. 8, a viscoelasticity measurement device 120 according to this embodiment includes an oscillator 21, a displacement sensor 22, a displacement detector 23, a bandpass filter 24, a frequency adjustment unit 25, an oscillation velocity computing unit 26, a gain adjustment unit 27, an amplifier 28, a driver 29, an actuator 30, a self-oscillation detection unit 32, a computing unit 33, and a memory 34.

The oscillator 21 is a structure having the mass M and made of a semiconductor material or the like. The material, shape, and the like of the oscillator 21 differ depending on the physical property and the like of the viscoelastic body as the measurement object. To measure the viscoelasticity of the viscoelastic body, the oscillator 21 is brought into contact with the viscoelastic body. In the case where the viscoelastic body is a thin film material such as a coating agent, the oscillator 21 is a structure whose cross section is rectangular (e.g. a cube) as an example, and one surface of the oscillator 21 is closely attached to the thin film. In the case where the viscoelastic body is a fluid, the oscillator 21 is shaped like a cantilever as an example, and its probe is inserted into the fluid. Alternatively, the oscillator 21 may be a cone, a cylinder, or the like as used in conventional rheometers.

The displacement sensor 22 is a sensor for detecting the displacement of the oscillator 21, and supplies the sensor output to the displacement detector 23.

The displacement detector 23 detects the displacement x of the oscillator 21 based on the sensor output from the displacement sensor 22, and supplies a displacement signal indicating the detected displacement x to the bandpass filter 24.

Examples of the displacement sensor 22 or the combination of the displacement sensor 22 and the displacement detector 23 include an electrostatic capacitance displacement sensor, an encoder, an optical displacement meter, and a strain gauge.

The bandpass filter 24 is a passing band variable filter. The bandpass filter 24 extracts a signal component of a passing frequency band (hereafter referred to as "specific frequency band") $fbw_i$ whose center frequency is a specific frequency $fp_i$ set by the frequency adjustment unit 25, and supplies the extracted signal component $x_i$ (hereafter referred to as "specific frequency component $x_i$") of the displacement signal to the oscillation velocity computing unit 26 and the self-oscillation detection unit 32.

Examples of the bandpass filter 24 include an analog filter, a digital filter, and a lock-in amplifier.

The frequency adjustment unit 25 sequentially switches between the n specific frequencies $fp_1$ to $fp_n$ in the measurement frequency range set according to the physical property and the like of the measurement object, and sets the passing frequency band of the bandpass filter 24 to one of specific frequency bands $fbw_1$ to $fbw_n$ whose center frequencies are respectively the specific frequencies $fp_1$ to $fp_n$. In detail, after setting an initial value (e.g., the specific frequency $fp_1$) of the specific frequencies $fp_1$ to $fp_n$, the frequency adjustment unit 25 sequentially changes the specific frequency to another frequency (e.g., the specific frequency $fp_i+1$) in response to a control signal from the self-oscillation detection unit 32.

The oscillation velocity computing unit 26 includes a differentiator. The oscillation velocity computing unit 26 differentiates the specific frequency component $x_i$ from the bandpass filter 24 by the differentiator to compute the oscillation velocity $dx_i/dt$ of the oscillator 21 corresponding to the specific frequency $fp_i$ and supplies computed $dx_i/dt$ to the amplifier 28.

The gain adjustment unit 27 sets, in response to a control signal from the frequency adjustment unit 25, an initial value of the linear velocity feedback gain $G_{lin}$ of the amplifier 28, and changes the gain $G_{lin}$ of the amplifier 28 each time the self-oscillation detection unit 32 completes the detection process for $G_{lin}$. In detail, each time the detection process for currently set $G_{lin}$ is completed, the gain adjustment unit 27 increases (or decreases) $G_{lin}$ by preset Δg. The gain adjustment is repeatedly performed until the self-oscillation detection unit 32 detects the self-oscillation of the oscillator 21 or the gain adjustment unit 27 reaches a preset upper limit (or lower limit) of the gain.

The amplifier 28 includes a variable amplifier. The amplifier 28 multiplies the linear velocity feedback gain $G_{lin}$ set by the gain adjustment unit 27 and the oscillation velocity $dx_i/dt$ supplied from the oscillation velocity computing unit 26, and supplies computed $G_{lin} \cdot dx_i/dt$ to the driver 29 as a feedback control signal Fs.

The driver 29 generates, based on the feedback control signal Fs supplied from the amplifier 28, a drive signal for driving the actuator 30 to apply a force Fv proportional to the motion velocity of the oscillator 21 to the oscillator 21, and supplies the generated drive signal to the actuator 30. For example, the driver 29 supplies the drive signal obtained by amplifying the feedback control signal Fs from the amplifier 28, to the actuator 30.

The actuator 30 applies, to the oscillator 21, the force Fv proportional to the motion velocity of the oscillator 21, based on the drive signal supplied from the driver 29. Examples of the actuator 30 include a motor, a piezo element, a voice coil, and an electrostatic actuator.

The self-oscillation detection unit 32 detects whether or not the oscillator 21 is self-oscillating, based on the specific frequency component (oscillation component) $x_i$ (or the oscillation velocity $dx_i/dt$, or the frequency spectrum of the oscillation amplitude). In the case of detecting that the oscillator 21 is self-oscillating, the self-oscillation detection unit 32 supplies the linear velocity feedback gain $G_{lin}$ at the time to the computing unit 33 as an oscillation limit gain $G_i^*$.

In the case where the linear velocity feedback gain $G_{lin}$ is changed, the oscillator 21 starts self-oscillation for the first time when the linear velocity feedback gain $G_{lin}$ reaches the oscillation limit. The oscillation limit gain which is the linear velocity feedback gain at the oscillation limit represents a viscosity equivalent value.

In detail, when the oscillation amplitude of the oscillator 21 is relatively small and the expression (14) holds true where the absolute value of the coefficient of dx/dt in the expression (14) is small, the oscillation frequency of the oscillator 21 is, in a linear oscillation theory, approximately equivalent to the linear natural frequency of the oscillator 21 that does not depend on the oscillation amplitude.

Suppose the linear velocity feedback gain $G_{lin}$ (>0) is increased gradually. When the condition of the following expression (17) is satisfied, the oscillation system becomes a negative damping system and self-oscillates.

$$C_{lin} - G_{lin} < 0 \quad (17)$$

Accordingly, the linear velocity feedback gain $G_{lin}^*$ (oscillation limit gain) that provides the oscillation limit of self-oscillation at which the oscillator 21 starts oscillation can be written as the following expression (18).

$$G_{lin}(=G_{lin}^*)=C_{lin} \quad (18)$$

Hence, the linear viscosity $C_{lin}$ can be identified by computing the linear velocity feedback gain $G_{lin}^*$ that provides the oscillation limit of self-oscillation.

The computing unit 33 computes $1/G_i^*$ which is the inverse of the oscillation limit gain $G_i^*$, in response to reception of the oscillation limit gain $G_i^*$ from the self-oscillation detection unit 32. The computing unit 33 also multiplies the specific frequency $fp_i$ from the frequency adjustment unit 25 by $2\pi$, to compute the angular frequency $\omega p_i$. Here, $\omega p_i$ is the angular frequency $\omega_s$ shown in the expression (15) corresponding to the combination of the added mass and the unit viscoelastic element having the self-oscillation frequency responsive to the specific frequency $fp_i$, and is written as $\omega p\{i\}=(K_i/M_i)^{1/2}$. Therefore, the square root of the ratio of the linear elastic modulus $K_i$ and the mass $M_i$ of the oscillator 21 can be found by computing $\omega p_i$. The computing unit 33 stores these computation results and the oscillation limit gain $G_i^*$ and the specific frequency $fp_i$ used in the computation, in the memory 34.

The memory 34 is a memory for storing the specific frequency $fp_i$ of the bandpass filter 24, the oscillation limit gain $G_i^*$ at the time of detection that the oscillator 21 is self-oscillating, and the angular frequency $\omega p_i$ ($=(K_i/M_i)^{1/2}$) and the inverse $1/G_i^*$ of the oscillation limit gain corresponding to the angular frequency $\omega p_i$ which are computed in the computing unit 33 based on the above-mentioned measurement values.

The viscoelasticity measurement device 120 in this embodiment includes a computer system for realizing each of the above-mentioned functions by software or for controlling hardware for realizing each of the above-mentioned functions, though not shown.

In detail, the viscoelasticity measurement device 120 includes: a central processing unit (CPU) performing various control and operations; a random access memory (RAM) functioning as a work memory; a read only memory (ROM) storing dedicated programs for realizing each of the above-mentioned functions, data necessary for executing the programs, and the like; and a data transmission bus for transmitting data to each component.

(Viscoelasticity Measurement Process)

Figure 9:
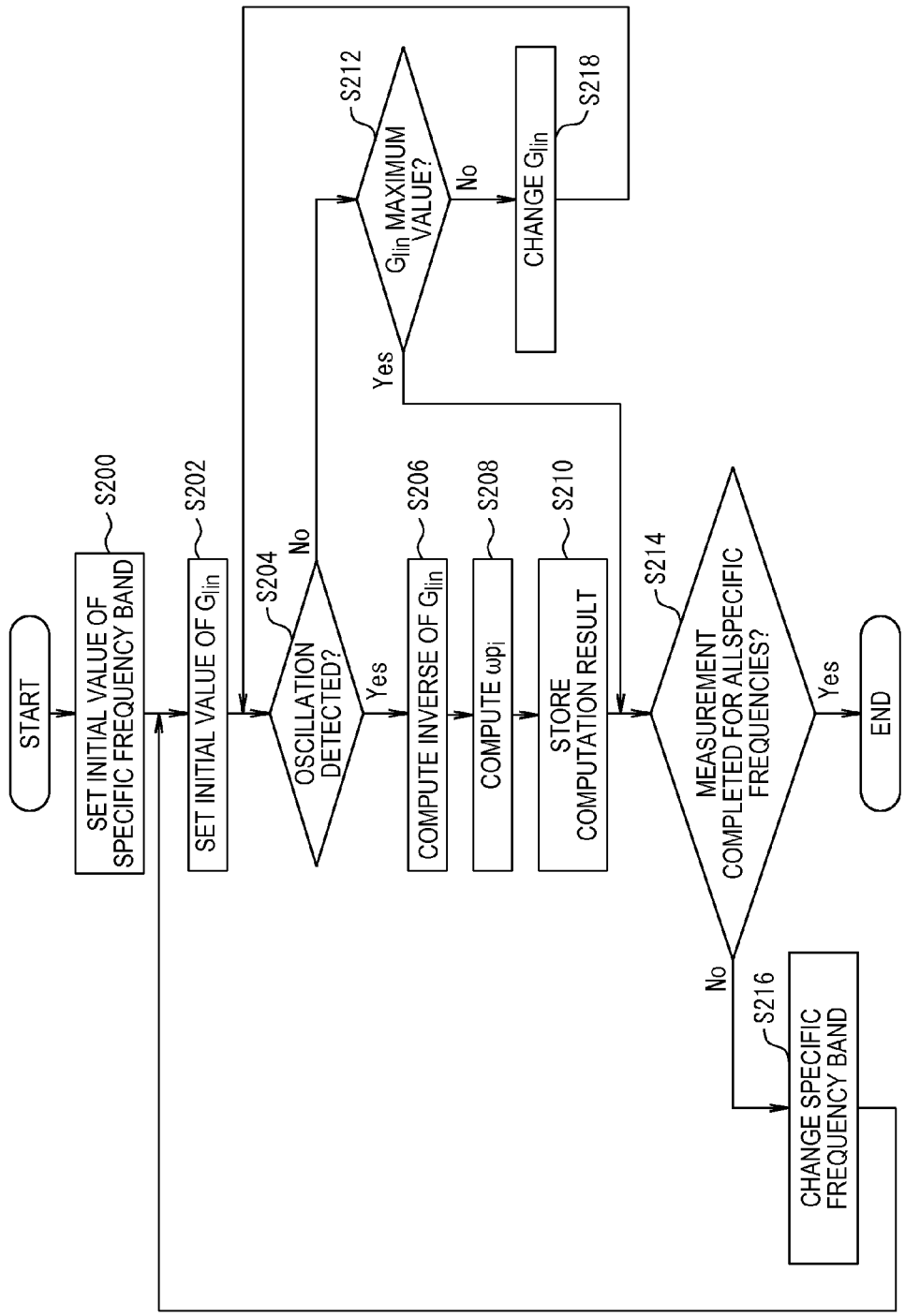
FIG. 9 is a flowchart showing an example of a procedure of a viscoelasticity measurement process.

The following describes a procedure of a viscoelasticity measurement process executed in the viscoelasticity measurement device 120, with reference to FIG. 9. FIG. 9 is a flowchart showing an example of the procedure of the viscoelasticity measurement process.

As shown in FIG. 9, the procedure first proceeds to step S200, and the frequency adjustment unit 25 sets the passing frequency band of the bandpass filter 24 to the initial value, and outputs a control signal to the gain adjustment unit 27. The procedure then proceeds to step S202. An example of the initial value is a band whose center frequency (or resonance frequency) is the lowest frequency (e.g., $fp_1$) in the measurement frequency range $fp_1$ to $fp_n$ set beforehand according to the physical property and the like of the viscoelastic body as the measurement object.

In step S202, the gain adjustment unit 27 sets the linear velocity feedback gain $G_{lin}$ of the amplifier 28 to the initial value, in response to the control signal from the frequency adjustment unit 25. The procedure then proceeds to step S204. The initial value may be any value.

In step S204, the self-oscillation detection unit 32 determines whether or not the oscillator 21 is oscillating (self-oscillating). In the case of determining that the oscillator 21 is oscillating (Yes), the self-oscillation detection unit 32 sets the linear velocity feedback gain $G_{lin}$ at the time as the oscillation limit gain $G_i^*$, and supplies $G_i^*$ to the computing unit 33. The procedure then proceeds to step S206. In the case where the self-oscillation detection unit 32 determines that the oscillator 21 is not oscillating (No), the procedure proceeds to step S212.

Whether or not the oscillator 21 is oscillating is determined as follows. For example, the self-oscillation detection unit 32 may determine that the oscillator 21 is oscillating, in the case where the oscillation displacement $x_i$ or the oscillation velocity $dx_i/dt$ changes by a preset threshold or more.

In the case where the procedure proceeds to step S206, the computing unit 33 computes the inverse $(1/G_i^*)$ of the oscillation limit gain in response to reception of the oscillation limit gain $G_i^*$ from the self-oscillation detection unit 32. The procedure then proceeds to step S208.

In step S208, the computing unit 33 acquires the specific frequency $fp_i$ from the frequency adjustment unit 25, and multiplies the acquired specific frequency $fp_i$ by $2\pi$, to compute the angular frequency $\omega p_i$. The procedure then proceeds to step S210.

In step S210, the computing unit 33 stores the oscillation limit gain $G_i^*$, the specific frequency $fp_i$, the inverse $(1/G_i^*)$ of the oscillation limit gain computed in step S206, and the angular frequency $\omega p_i$ computed in step S208, in the memory 34. The procedure then proceeds to step S214.

In the case where no oscillation is detected in step S204 and the procedure proceeds to step S212, the gain adjustment unit 27 determines whether or not the linear velocity feedback gain $G_{lin}$ of the amplifier 28 is set to a maximum value. In the case where the gain adjustment unit 27 determines that the linear velocity feedback gain $G_{lin}$ is set to the maximum value (Yes), the procedure proceeds to step S214. In the case where the gain adjustment unit 27 determines that the linear velocity feedback gain $G_{lin}$ is not set to the maximum value (No), the procedure proceeds to step S218.

In the case where the procedure proceeds to step S214, the frequency adjustment unit 25 determines whether or not the measurement is completed for all specific frequencies $fp_i$. In the case where the frequency adjustment unit 25 determines that the measurement is completed for all specific frequencies $fp_i$ (Yes), the process ends. In the case where frequency adjustment unit 25 determines that the measurement is not completed for all specific frequencies $fp_i$ (No), the procedure proceeds to step S216.

In the case where the procedure proceeds to step S216, the frequency adjustment unit 25 changes the specific frequency band of the bandpass filter 24 to another unmeasured frequency band, and outputs a control signal to the gain adjustment unit 27. The procedure then proceeds to step S202.

In the case where the gain adjustment unit 27 determines that the linear velocity feedback gain $G_{lin}$ is not set to the maximum value in step S212 and the procedure proceeds to step S218, the gain adjustment unit 27 increases the current linear velocity feedback gain $G_{lin}$ set in the amplifier 28, by preset $\Delta g$. The procedure then proceeds to step S204.

Here, $\Delta g$ is set to such a relatively small value that allows the oscillation frequency $fp_i$ to be detected from the oscillation displacement $x_i$ of the oscillator 21, when the linear velocity feedback gain $G_{lin}$ is kept at "$G_{lin}+\Delta g$". When $\Delta g$ is larger, the linear velocity feedback gain $G_{lin}$ is larger, causing the oscillation amplitude of the oscillator 21 to increase. As a result, the oscillation frequency $fp_i$ of the oscillator 21 deviates from the linear natural frequency, and the oscillation frequency $fp_i$ easily varies with a slight change in oscillation amplitude. Accordingly, $\Delta g$ is preferably as small as possible.

(Operation)

Figure 10:
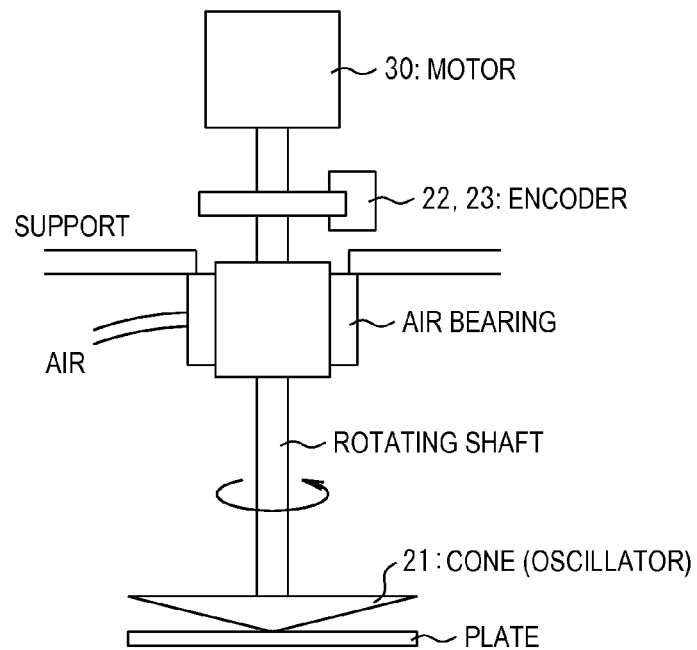
FIG. 10 is a diagram showing an example of the device structure of the viscoelasticity measurement device according to Embodiment 2 of the present invention.

The following describes the operation of the viscoelasticity measurement device 120 in this embodiment, with reference to FIG. 10.

FIG. 10 is a diagram showing an example of the device structure of the viscoelasticity measurement device 120 in this embodiment.

In the device structure shown in FIG. 10, a fixed disk (plate) and a conic structure (hereafter referred to as "cone 21") as the oscillator 21 are placed so that the cone 21 faces the upper surface of the plate with the apex of the cone 21 pointing downward. A liquid or solid measurement sample (viscoelastic body) is inserted between the plate and the cone 21.

A rotating shaft concentric to the cone 21 is provided on the bottom surface of the cone 21, and rotatably supported by an air bearing. A motor (hereafter referred to as "motor 30") as the actuator 30 is connected to the rotating shaft. The motor 30 applies rotation oscillation to the cone 21, and an encoder (hereafter referred to as "encoder 22, 23") as the displacement sensor 22 and the displacement detector 23 detects the displacement of the cone 21. The bandpass filter 24 (not shown) limits the frequency of the output of the encoder 22, 23, and the oscillation velocity computing unit 26 (not shown) computes the velocity $dx_i/dt$ and supplies it to the amplifier 28 (not shown). The amplifier 28 multiplies the velocity $dx_i/dt$ by the linear velocity feedback gain $G_{lin}$, and supplies the linear velocity feedback signal Fs as the multiplication result to a motor drive circuit 29 (not shown) as the driver 29. As a result of the output of the encoder 22, 23 passing through the motor drive circuit 29, the motor 30 generates the force Fv proportional to the motion velocity of the cone 21.

The following describes the operation of the viscoelasticity measurement device 120 having the device structure shown in FIG. 10.

Before the measurement, the sample is inserted between the plate and the cone 21. The power switch of each component is then turned on.

When supplied with power, the viscoelasticity measurement device 120 starts a control program for viscoelasticity measurement stored in the ROM by the CPU. First, the frequency adjustment unit 25 sets the specific frequency band, which is the passing frequency band of the bandpass filter 24, to the band $fbw_1$ whose center frequency is the preset initial value (e.g., the specific frequency $fp1$) out of the specific frequencies $fp_1$ to $fp_n$ in the preset measurement frequency range (step S200). The bandpass filter 24 accordingly allows the signal component of the specific frequency band $fbw_1$ to pass through from among the signal components of the displacement signal indicating the displacement x of the oscillator and supplied from the encoder 22, 23, and restricts the passage of (attenuates) the signal components of the other frequency bands. In other words, the bandpass filter 24 extracts the signal component $x_i$ of the specific frequency band $fbw_1$ from the displacement signal of the displacement $x_i$ and supplies the extracted specific frequency component $x_i$ to the oscillation velocity computing unit 26 and the self-oscillation detection unit 32. Having set the specific frequency band of the bandpass filter 24, the frequency adjustment unit 25 outputs a control signal to the gain adjustment unit 27.

The gain adjustment unit 27 sets the linear velocity feedback gain $G_{lin}$ of the amplifier 28 to the preset initial value (small value) in response to the control signal from the frequency adjustment unit 25 (step S202).

In an initial stage after the initial value is set, the oscillator 21 is not displaced, so that the displacement x detected by the encoder 22, 23 and the specific frequency component $x_i$ extracted by the bandpass filter 24 are 0, and the oscillation velocity $dx_i/dt$ is 0. Actually, however, the displacement x and the specific frequency component $x_i$ are not 0 and have some value due to noise in the surrounding environment and the like. The encoder detects this displacement x, the bandpass filter 24 extracts the specific frequency component $x_i$ from the displacement signal of the displacement x, and the oscillation velocity computing unit 26 computes the oscillation velocity $dx_i/dt$ from the extracted specific frequency component $x_i$. The oscillation velocity computing unit 26 supplies the oscillation velocity $dx_i/dt$ to the amplifier 28. The amplifier 28 multiplies the oscillation velocity $dx_i/dt$ and the set linear velocity feedback gain $G_{lin}$, and supplies the multiplication result $G_{lin} \cdot dx_i/dt$ to the motor drive circuit 29 as the feedback control signal Fs.

In the case where, in the initial stage of self-oscillation, the displacement of the cone 21 merely caused by noise in the surrounding environment and the like is less than the detection lower limit of the encoder 22, 23, oscillation of a given frequency is applied preliminarily. In detail, the cone 21 is caused to oscillate at a given constant frequency.

The motor drive circuit 29 generates the drive signal for the motor 30 for applying the force Fv proportional to the oscillation velocity $dx_i/dt$ of the cone 21 to the cone 21, based on the feedback control signal Fs received from the amplifier 28. The motor drive circuit 29 supplies the generated drive signal to the motor 30. The motor 30 is driven by the drive signal, and applies the force Fv to the cone 21. A feedback loop is thus formed, and the force Fv proportional to the oscillation velocity of the cone 21 is applied to the cone 21.

Based on the specific frequency component $x_i$ (hereafter referred to as "oscillation displacement $x_i$") supplied from the bandpass filter 24, the self-oscillation detection unit 32 compares the oscillation displacement $x_i$ with a preset threshold. The self-oscillation detection unit 32 determines whether or not the cone 21 is oscillating based on the comparison result (step S204). In the case where the oscillation displacement $x_i$ is less than the threshold and the cone 21 is determined as not oscillating (step S204: No), the self-oscillation detection unit 32 supplies a signal indicating that the cone 21 is not oscillating, to the gain adjustment unit 27. The gain adjustment unit 27 accordingly determines whether or not the current value of the linear velocity feedback gain $G_{lin}$ is the maximum value (step S212). In the case of determining that the current value of the linear velocity feedback gain $G_{lin}$ is not the maximum value (step S212: No), the gain adjustment unit 27 increases the linear velocity feedback gain $G_{lin}$ of the amplifier 28 by $\Delta g$ (step S218). This increase process is performed each time the oscillation displacement xi is determined as less than the threshold and $G_{lin}$ is determined as not the maximum value.

When the linear velocity feedback gain $G_{lin}$ is gradually increased in this way, $G_{lin}$ eventually exceeds the proportionality constant $c_i$ of the viscous force of the mechanical element having the self-oscillation frequency responsive to the specific frequency band $fbw_i$ (specific frequency $fp_i$) set in the bandpass filter 24. Self-oscillation occurs at this point.

In the case of detecting self-oscillation (step S204: Yes), the self-oscillation detection unit 32 supplies the current linear velocity feedback gain (oscillation limit gain) $G_i^*$ as the limit at which self-oscillation occurs, to the computing unit 33.

The computing unit 33 computes the inverse $1/G_i^*$ of the oscillation limit gain $G_i^*$ (step S206). The computing unit 33 also acquires the specific frequency $fp_i$ at the time from the frequency adjustment unit 25, and multiplies the acquired specific frequency $fp_i$ by $2\pi$, to compute the angular frequency $\omega p_i$ (step S208). The computing unit 33 stores these computation results, and the oscillation limit gain $G_i^*$ and the specific frequency $fp_i$ corresponding to the computation results, in the memory 34 (step S210).

Though the structure in which the inverse $1/G_i^*$ of the oscillation limit gain and the angular frequency $\omega p_i$ are computed and stored in the memory 34 each time the oscillation limit gain $G_i^*$ is measured is described here, the present invention is not limited to this structure. For example, the following structure is also available. The oscillation limit gains $G_1^*$ to $G_n^*$ corresponding to the specific frequencies and the specific frequencies $fp_1$ to $fp_n$ corresponding to these oscillation limit gains are sequentially stored in the memory 34 first. Then, after the measurement is completed for all specific frequencies, the inverse $1/G_i^*$ of the oscillation limit gain and the angular frequency $\omega p_i$ are computed from the measurement results stored in the memory 34.

In the case where there is any unmeasured specific frequency (step S214: No), the frequency adjustment unit 25 changes, for example, the current specific frequency band $fbw_1$ of the bandpass filter 24 to another specific frequency band $fbw_2$ whose center frequency is the unmeasured specific frequency $fp_2$ (step S216). The bandpass filter 24 accordingly allows the signal component of the specific frequency band $fbw_2$ whose center frequency is the changed specific frequency $fp_2$ to pass through from among the signal components of the displacement signal output from the encoder 22, 23, and restricts the passage of the signal components of the other frequency bands.

The same process (the process of steps S202 to S216) is repeatedly performed. In the case where the measurement is determined as being completed for all of the specific frequencies $fp_1$ to $fp_n$ (step S214: Yes), the measurement ends.

Note that $1/G_i^*$ and "$\omega p_i=(K_i/M_i)^{1/2}$" stored in the memory 34 are graphed so that the vertical axis represents $1/G_i^*$ and the horizontal axis represents $\omega p_i$, to form a viscoelastic spectrum by self-oscillation corresponding to the measurement sample.

As described above, the viscoelasticity measurement method and the viscoelasticity measurement device 120 in this embodiment enable the following. The signal component of the specific frequency is extracted by the bandpass filter 24 from the displacement signal indicating the oscillation displacement of the oscillator 21 in contact with the viscoelastic body, and the oscillation displacement of the extracted specific frequency component is differentiated to compute the oscillation velocity corresponding to the specific frequency component. The oscillation velocity is then multiplied by the linear velocity feedback gain to compute the feedback control signal Fs. By feedback control using computed Fs, the force Fv proportional to the oscillation velocity of the oscillator 21 is applied to the oscillator 21, to cause the oscillator 21 to self-oscillate. Moreover, the passing band (specific frequency) of the bandpass filter 24 is changed, and the feedback gain is changed for the changed specific frequency. Whether or not the oscillator is self-oscillating is detected each time the feedback control using the changed feedback gain is performed. The feedback gain (oscillation limit gain) at the time of detection of self-oscillation is measured for the changed specific frequency. Further, the inverse of the measured oscillation limit gain is computed from the measured oscillation limit gain, and the angular frequency is computed from the specific frequency. The viscoelastic spectrum of the viscoelastic body is obtained by graphing the oscillation limit gain in the vertical axis and the angular frequency in the horizontal axis.

Thus, even in the case where the viscoelastic body has complex viscoelasticity unable to be represented by a simple mechanical model, the frequency spectrum of viscoelasticity effective in estimating the internal properties of the viscoelastic body can be measured while clearly distinguishing elasticity and viscosity.

In the foregoing embodiment, the displacement sensor 22 and the displacement detector 23 constitute a displacement sensor, the bandpass filter 24 constitutes a specific frequency component extraction unit, and the amplifier 28 and the driver 29 constitute a feedback control unit.

In the foregoing embodiment, the oscillation velocity computing unit 26 constitutes an oscillation velocity detection unit, and the computing unit 33 and the memory 34 constitute a viscoelasticity measurement unit.

In the foregoing embodiment, step S204 corresponds to a step of detecting whether or not the oscillator is self-oscillating, step S216 corresponds to a step of changing the specific frequency, and step S218 corresponds to a step of changing a linear velocity feedback gain.

In the foregoing embodiment, steps S206 to S210 correspond to a step of measuring viscoelasticity.

Embodiment 3

Figure 11:
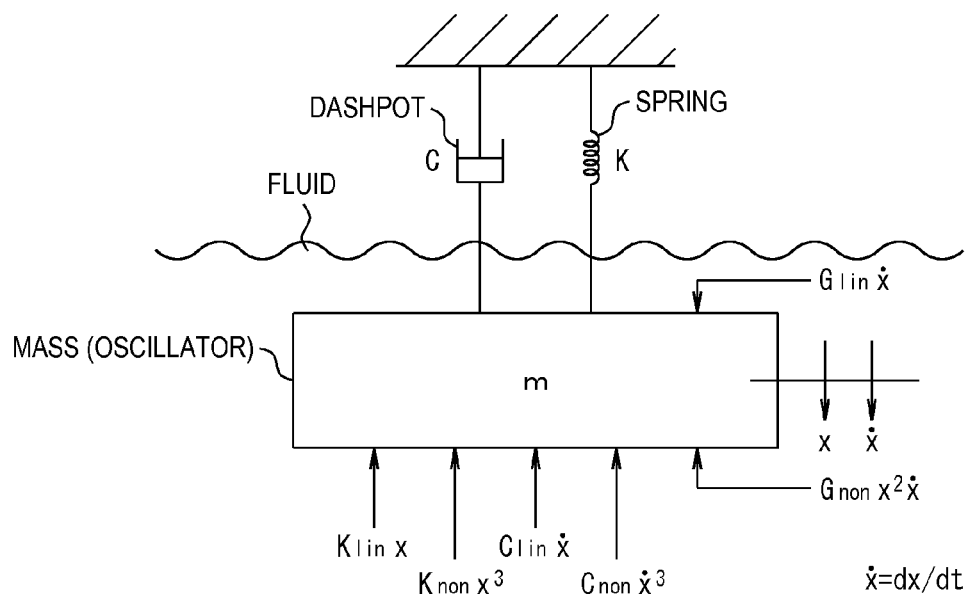
FIG. 11 is a schematic diagram of a mechanical system illustrative of the relations between a viscoelastic body, an oscillator, an actuator, and a displacement sensor according to Embodiment 3 of the present invention.
Figure 12:
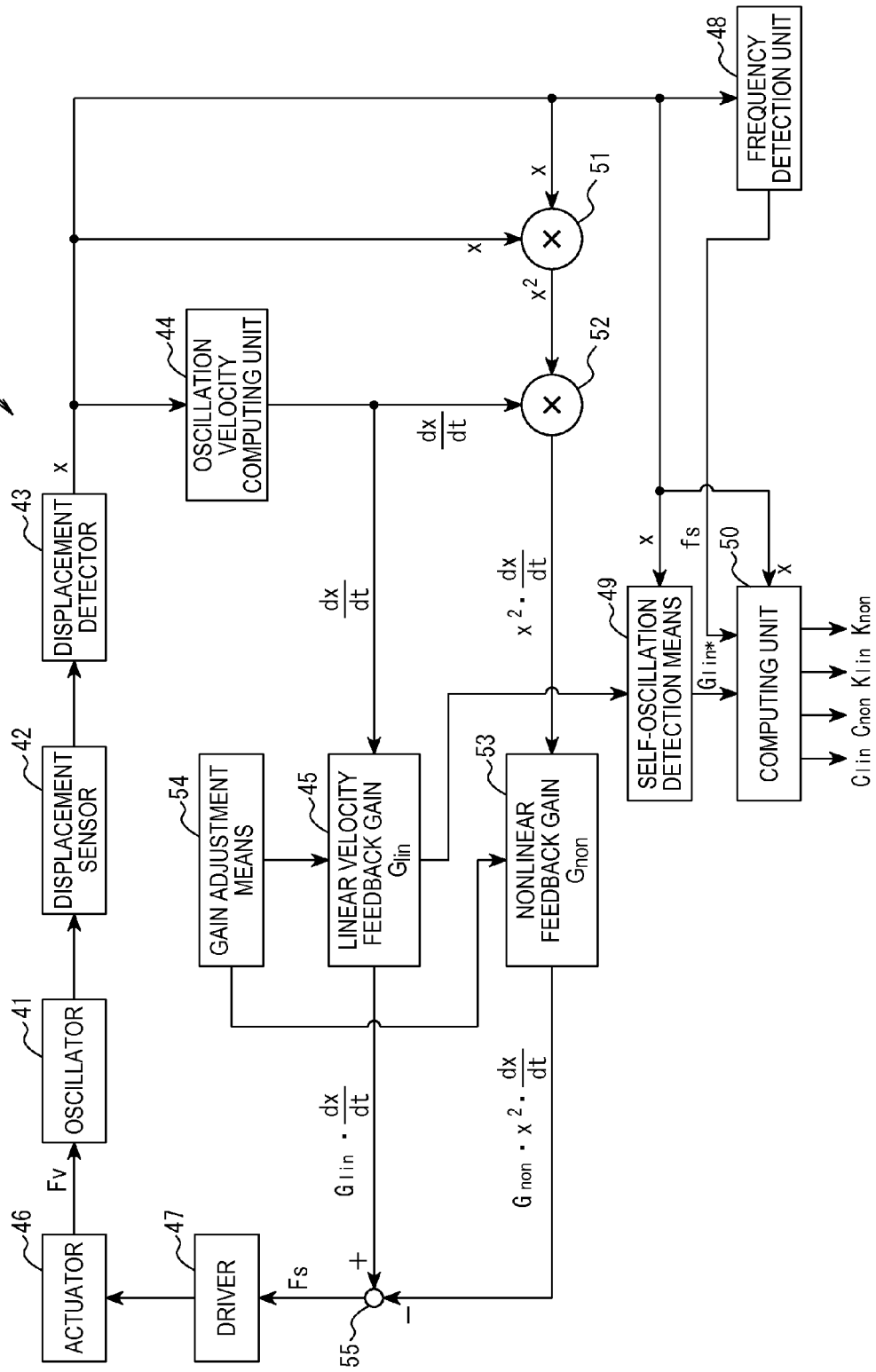
FIG. 12 is a schematic block diagram showing an example of a viscoelasticity measurement device.
Figure 13:
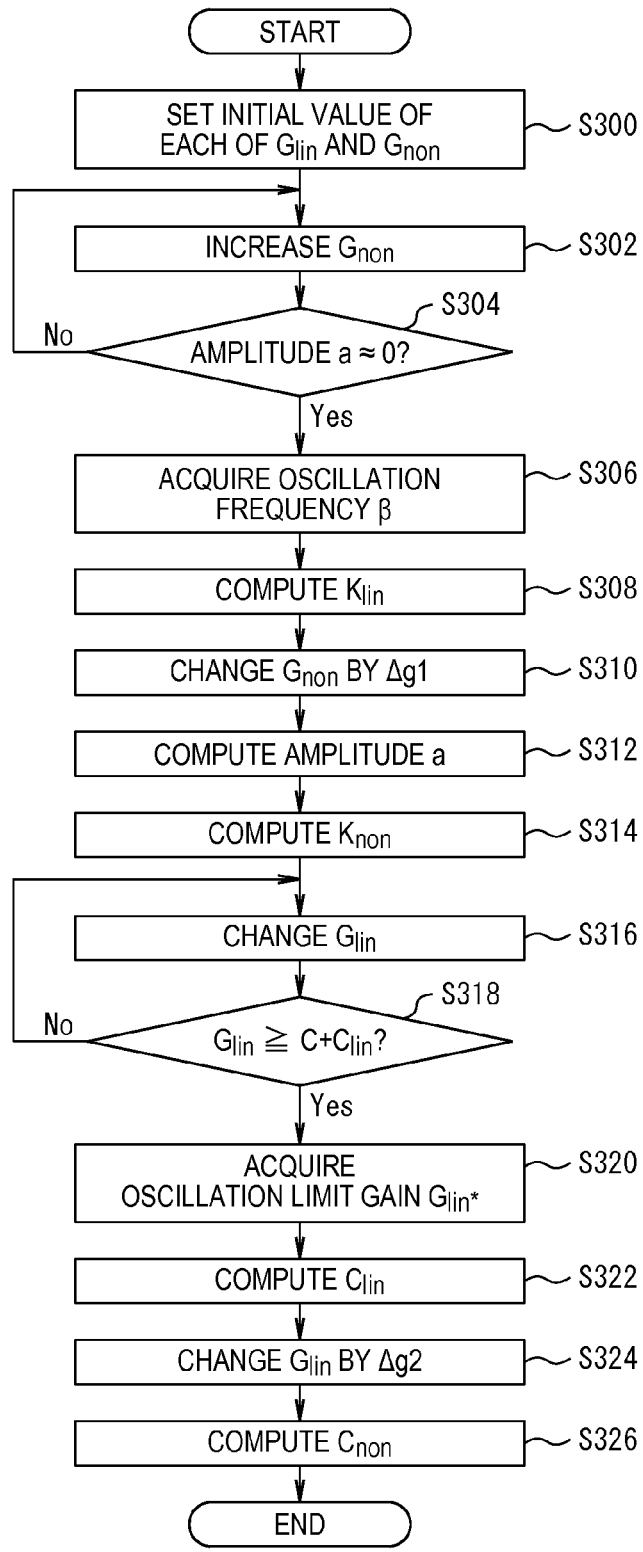
FIG. 13 is a flowchart showing an example of a procedure of a viscoelasticity measurement process.

The following describes Embodiment 3 of a viscoelasticity measurement method and a viscoelasticity measurement device according to the present invention, with reference to drawings. FIGS. 11 to 13 are diagrams showing Embodiment 3 of the viscoelasticity measurement method and the viscoelasticity measurement device according to the present invention.

(Structure)

FIG. 11 is a schematic diagram of a mechanical system illustrative of the relations between an oscillator, a viscoelastic body, an actuator, and a displacement sensor according to this embodiment.

The viscoelasticity measurement method in this embodiment is a method of measuring the linear elasticity, nonlinear elasticity, linear viscosity, and nonlinear viscosity of a viscoelastic body having both viscosity and elasticity, which is a measurement object. To realize such a method, a viscoelasticity measurement device that includes: an oscillator (e.g., a cantilever) brought into contact with a viscoelastic body; an actuator for applying a force to the oscillator; control means for feedback-controlling the actuator using linear and nonlinear feedback gains; a displacement sensor for measuring the displacement x of the oscillator; a conversion circuit for differentiating the signal of the displacement sensor to convert it to a velocity output; and a measurement device for measuring the oscillation frequency of the oscillator.

Here, the oscillator according to this embodiment can be replaced by a spring-mass-dashpot system (a single-degree-of-freedom secondary resonance system). In other words, the oscillator may be realized by any concrete method, so long as it can be modeled by a spring-mass-dashpot system (a single-degree-of-freedom secondary resonance system). For example, a cantilever modeled only in a primary oscillation mode may be used.

The mechanical model shown in FIG. 11 is an exemplary structure in which the oscillator is inserted into a fluid having both viscosity and elasticity.

In the mechanical model in FIG. 11, the oscillator has a structure in which a spring with an elastic constant K and a dashpot with a damping constant C are connected in parallel, and one end of each of the spring and the dashpot is fixed and the other end connected to a mass M (oscillator).

In this embodiment, in a state where the oscillator is inserted in the fluid, the actuator is driven and feedback-controlled by a linear velocity feedback control signal obtained by multiplying a linear velocity feedback gain $G_{lin}$ and an oscillation velocity dx/dt and a nonlinear feedback control signal obtained by multiplying a nonlinear feedback gain $G_{non}$, the square of the displacement x, and the oscillation velocity dx/dt, as shown in FIG. 11.

In detail, a feedback control signal Fb shown in the following expression (19) is computed, and the actuator is driven and feedback-controlled based on computed Fb.

$$Fb=(G_{lin}-G_{non}\cdot x^2)\cdot(dx/dt) \qquad (19).$$

In the expression (19), Fb is the feedback control signal, $G_{lin}$ is the linear velocity feedback gain which is a positive value, $G_{non}$ is the nonlinear feedback gain, which is a positive value, x is the displacement of the oscillator, and dx/dt is the oscillation velocity of the oscillator.

Through the oscillator that self-oscillates according to such feedback control, a linear elastic force $K_{lin}x$, a nonlinear elastic force $K_{non}x^3$, a linear viscous force $C_{lin}(dx/dt)$, and a nonlinear viscous force $C_{non}(dx/dt)^3$ act on the viscoelastic body as the measurement object.

In such dynamics, an equation of motion shown in the following expression (20) holds.

$$M(d^2x/dt^2)+C(dx/dt)+Kx=-K_{lin}x-K_{non}x^3-C_{lin}(dx/dt)-C_{non}(dx/dt)^3+G_{lin}(dx/dt)-G_{non}x^2(dx/dt) \qquad (20).$$

In the expression (20), M is the mass of the oscillator, C is the damping constant of the oscillator, K is the spring constant of the oscillator, $C_{lin}$ is the linear viscosity of the measurement object, $C_{non}$ is the nonlinear viscosity of the measurement object, $K_{lin}$ is the linear elastic modulus of the measurement object, and $K_{non}$ is the nonlinear elastic modulus of the measurement object.

Suppose the mass M, the damping constant C, and the spring constant K of the oscillator are known, as the oscillator is designed by the measurer. Likewise, $G_{lin}$ and $G_{non}$ are known as they are set by the measurer.

Making the expression (20) dimensionless yields the following expression (21).

$$(d^2x/dt^2)+C(dx/dt)+x=-K_{lin}x-K_{non}x^3-C_{lin}(dx/dt)-C_{non}(dx/dt)^3 G_{lin}(dx/dt)-G_{non}x^2(dx/dt) \qquad (21).$$

Transposing and rearranging the expression (21) yields the following expression (22).

$$(d^2x/dt^2)+(C+C_{lin}-G_{lin}+G_{non}x^2)(dx/dt)+C_{non}(dx/dt)^3+(1+K_{lin})x+K_{non}x^3=0 \qquad (22).$$

The expression (22) is solved using a method of multiple scale to determine steady-state solutions. The following expressions (23) to (25) are obtained as a result.

$$x=a\cdot\cos((\beta+3K_{non}a^2/8\beta)t+C') \qquad (23)$$

$$a=2((G_{lin}C-C_{lin})/(3C_{non}\beta2+G_{non}))^{1/2} \qquad (24)$$

$$\beta^2=1+K_{lin} \qquad (25).$$

In the expression (23), C' is an integration constant determined from an initial condition.

In this embodiment, the linear velocity feedback gain $G_{lin}$ and the nonlinear feedback gain $G_{non}$ are controlled to measure the linear viscosity $C_{lin}$, the nonlinear viscosity $C_{non}$, the linear elastic modulus $K_{lin}$, and the nonlinear elastic modulus $K_{non}$ of the measurement object, based on the expressions (23) to (25). The linear and nonlinear viscosity and elasticity of the measurement object indicated by $C_{lin}$, $C_{non}$, $K_{lin}$, and $K_{non}$ are hereafter collectively referred to as "viscoelasticity".

The following describes the schematic structure of the viscoelasticity measurement device according to this embodiment, with reference to FIG. 12. FIG. 12 is a schematic block diagram showing an example of the viscoelasticity measurement device according to this embodiment.

As shown in FIG. 12, a viscoelasticity measurement device 140 includes an oscillator 41, a displacement sensor 42, a displacement detector 43, an oscillation velocity computing unit 44, an amplifier 45, an actuator 46, a driver 47, a frequency detection unit 48, a self-oscillation detection unit 49, a computing unit 50, multipliers 51 and 52, an amplifier 53, a gain adjustment unit 54, and a computing unit 55.

The oscillator 41 is a structure having the mass M and made of a semiconductor material or the like. The material, shape, and the like of the oscillator 41 differ depending on the physical property and the like of the viscoelastic body as the measurement object. To measure the viscoelasticity of the viscoelastic body, the oscillator 41 is brought into contact with the viscoelastic body. In the case where the viscoelastic body is a thin film material such as a coating agent, the oscillator 41 is a structure whose cross section is rectangular (e.g., a cube) as an example, and one surface of the oscillator 41 is closely attached to the thin film. In the case where the viscoelastic body is a fluid, the oscillator 41 is shaped like a cantilever as an example, and its probe is inserted into the fluid.

The displacement sensor 42 is a sensor for detecting the displacement of the oscillator 41, and supplies the sensor output to the displacement detector 43.

The displacement detector 43 detects the displacement x of the oscillator 41 based on the sensor output from the displacement sensor 42, and supplies the detected displacement x to the oscillation velocity computing unit 44, the frequency detection unit 48, the self-oscillation detection unit 49, the computing unit 50, and the multipliers 51 and 52.

Examples of the displacement sensor 42 or the combination of the displacement sensor 42 and the displacement detector 43 include an electrostatic capacitance displacement sensor, an encoder, an optical displacement meter, and a strain gauge.

The oscillation velocity computing unit 44 includes a differentiator. The oscillation velocity computing unit 44 differentiates the displacement x from the displacement detector 43 by the differentiator to compute the oscillation velocity dx/dt of the oscillator 41, and supplies computed dx/dt to the amplifier 45 and the multiplier 52.

The gain adjustment unit 54 sets an initial value of the linear velocity feedback gain $G_{lin}$ of the amplifier 45, and sets an initial value of the nonlinear feedback gain $G_{non}$ of the amplifier 53. The gain adjustment unit 54 selectively changes one of the linear velocity feedback gain $G_{lin}$ of the amplifier 45 and the nonlinear feedback gain $G_{non}$ of the amplifier 53, in response to a command signal.

The amplifier 45 includes a variable amplifier. The amplifier 45 multiplies the linear velocity feedback gain $G_{lin}$ set by the gain adjustment unit 54 and the oscillation velocity dx/dt supplied from the oscillation velocity computing unit 44, and supplies computed $G_{lin}$·dx/dt to the computing unit 55.

The multiplier 51 multiplies two displacements x from the displacement detector 43 to compute $x^2$, and supplies computed $x^2$ to the multiplier 52.

The multiplier 52 multiplies $x^2$ from the multiplier 51 and the oscillation velocity dx/dt from the oscillation velocity computing unit 44 to compute $x^2$·dx/dt, and supplies computed $x^2$·dx/dt to the amplifier 53.

The amplifier 53 includes a variable amplifier. The amplifier 53 multiplies the nonlinear feedback gain $G_{non}$ set by the gain adjustment unit 54 and $x^2$·dx/dt supplied from the multiplier 52, and supplies computed $G_{non}$·$x^2$·dx/dt to the computing unit 55.

The computing unit 55 subtracts $G_{non}$·$x^2$·dx/dt supplied from the amplifier 53 from $G_{lin}$·dx/dt supplied from the amplifier 45 to compute a feedback control signal Fb (=($G_{lin}$−$G_{non}$·$x^2$)·dx/dt), and supplies computed Fb to the driver 47.

The driver 47 generates a drive signal based on the feedback control signal Fb supplied from the amplifier 53, and supplies the generated drive signal to the actuator 46.

The actuator 46 applies the force Fv to the oscillator 41 based on the drive signal supplied from the driver 47. Examples of the actuator 46 include a piezo element, a voice coil motor, and an electrostatic actuator.

The frequency detection unit 48 detects the frequency of the oscillation waveform formed by the displacement x based on the displacement x of the oscillator 41 supplied from the displacement detector 43. The frequency detection unit 48 supplies the detected frequency $f_s$ to the computing unit 50.

Examples of the frequency detection unit 48 include a frequency counter, an FFT analyzer, and a spectrum analyzer.

The self-oscillation detection unit 49 detects whether or not the oscillator 41 is self-oscillating, based on the oscillation displacement x (or the oscillation velocity dx/dt, or the frequency spectrum of the oscillation amplitude). In the case of detecting that the oscillator 41 is self-oscillating, the self-oscillation detection unit 49 supplies the linear velocity feedback gain $G_{lin}$ at the time to the computing unit 50 as an oscillation limit gain $G_{lin}^*$.

The computing unit 50 computes the linear viscosity $C_{lin}$, the nonlinear viscosity $C_{non}$, the linear elastic modulus $K_{lin}$, and the nonlinear elastic modulus $K_{non}$ of the measurement object, based on the displacement x when the gain adjustment unit 54 changes $G_{lin}$ or $G_{non}$, the physical quantity relating to the oscillation of the oscillator 41 such as the frequency $f_s$, the oscillation limit gain $G_{lin}^*$, and the expressions (23) to (25).

The viscoelasticity measurement device 140 in this embodiment includes a computer system for realizing each of the above-mentioned functions by software or for controlling hardware for realizing each of the above-mentioned functions, though not shown.

In detail, the viscoelasticity measurement device 140 includes: a central processing unit (CPU) performing various control and operations; a random access memory (RAM) functioning as a work memory; a read only memory (ROM) storing dedicated programs for realizing each of the above-mentioned functions, data necessary for executing the programs, and the like; and a data transmission bus for transmitting data to each component.

(Viscoelasticity Measurement Process)

The following describes a procedure of a viscoelasticity measurement process executed in the viscoelasticity measurement device 140, with reference to FIG. 13. FIG. 13 is a flowchart showing an example of the procedure of the viscoelasticity measurement process.

As shown in FIG. 13, the procedure first proceeds to step S300, and the gain adjustment unit 54 sets each of the linear velocity feedback gain $G_{lin}$ of the amplifier 45 and the nonlinear feedback gain $G_{non}$ of the amplifier 53 to the initial value. The procedure then proceeds to step S302. The initial value of each of $G_{lin}$ and $G_{non}$ may be any value.

In step S302, the gain adjustment unit 54 increases the nonlinear feedback gain $G_{non}$. The procedure then proceeds to step S304.

In step S304, the computing unit 50 computes the oscillation amplitude a of the oscillator 41, based on the displacement x when $G_{non}$ is increased. The computing unit 50 compares the computed oscillation amplitude a with a preset amplitude threshold. In the case where the computing unit 50 determines that the oscillation amplitude a is about equal to 0 ($a^2 \approx 0$ in a precise sense) based on the comparison result (Yes), the procedure proceeds to step S306. Otherwise (No), the procedure proceeds to step S302. For example, the computing unit 50 determines that the oscillation amplitude $a \approx 0$ in the case where the oscillation amplitude a is less than or equal to the oscillation threshold, and otherwise determines that the oscillation amplitude a is not about equal to 0 in the case where the oscillation amplitude a is greater than the oscillation threshold. The present invention is not limited to the structure in which the computing unit 50 computes the oscillation amplitude a from the displacement x of the oscillator 41. If the frequency detection unit 48 is capable of measuring the oscillation amplitude a, the computing unit 50 may acquire the oscillation amplitude a from the frequency detection unit 48.

In the case where the procedure proceeds to step S306, the computing unit 50 acquires the frequency $f_s$ from the frequency detection unit 48 at the time of determination that the oscillation amplitude a≈0. The procedure then proceeds to step S308.

The term (β+3K$_{non}$a$^2$/8β) in the expression (23) is the oscillation angular frequency of the oscillator 41, as shown in the following expression (26).

$$\omega_s = \beta + 3K_{non}a^2/8\beta \quad (26).$$

By setting the oscillation amplitude a≈0 in the expression (26), the frequency component can be limited to β alone. In detail, the nonlinear feedback gain G$_{non}$ is increased to decrease a$^2$ so that the expression (26) approximates to β. Thus, β(=2πf$_s$*) can be measured by measuring the oscillation frequency f$_s$* when the oscillation amplitude a≈0.

In step S308, the computing unit 50 computes the linear elastic modulus K$_{lin}$ of the measurement object from the expression (25) using the oscillation angular frequency β measured in step S306, and stores computed K$_{lin}$ in a memory (e.g., the RAM). The procedure then proceeds to step S310.

In step S310, the gain adjustment unit 54 changes the nonlinear feedback gain G$_{non}$ of the amplifier 53 by preset Δg1, from the state where the oscillation amplitude a≈0. The procedure then proceeds to step S312.

When G$_{non}$ is changed, the oscillation amplitude a changes, and the oscillation angular frequency ω$_s$ given by the expression (26) changes.

In step S312, the computing unit 50 computes the oscillation amplitude a from the oscillation displacement x of the oscillator 41 after G$_{non}$ is changed by Δg1. The procedure then proceeds to step S314.

In step S314, the computing unit 50 acquires the oscillation frequency f$_s$ from the frequency detection unit 48, and computes the oscillation angular frequency ω$_s$. Since β and the oscillation amplitude a are now known, the computing unit 50 computes the nonlinear elastic modulus K$_{non}$ of the measurement object from the expression (26), and stores computed K$_{non}$ in the memory. The procedure then proceeds to step S316.

In step S316, the gain adjustment unit 54 changes the linear velocity feedback gain G$_{lin}$ of the amplifier 45. The procedure then proceeds to step S318. Here, G$_{lin}$ is increased or decreased by preset Δg, according to the current value of G$_{lin}$. Alternatively, G$_{lin}$ is set to a relatively small value, and then increased by Δg.

In step S318, the self-oscillation detection unit 49 compares G$_{lin}$ and C+C$_{lin}$ based on the numerator part (G$_{lin}$−C−C$_{lin}$) in the expression (24). In the case where the self-oscillation detection unit 49 determines that "G$_{lin}$≥C+C$_{lin}$" (Yes), the procedure proceeds to step S320. Otherwise (No), the procedure proceeds to step S316.

When the oscillation amplitude of the oscillator 41 is relatively small and the expression (22) holds true where the absolute value of the coefficient of dx/dt in the expression (22) is small, the oscillation frequency of the oscillator 41 is, in a linear oscillation theory, approximately equivalent to the linear natural frequency of the oscillator 41 that does not depend on the oscillation amplitude.

When the linear velocity feedback gain G$_{lin}$ is changed and the condition "G$_{lin}$>C+C$_{lin}$" is satisfied, the oscillation system becomes a negative damping system and self-oscillates.

That is, when the linear velocity feedback gain G$_{lin}$ exceeds the constant C+C$_{lin}$ of the viscous term in the expression (24), a negative viscous term is generated, and the viscoelastic body self-oscillates. Hence, whether or not "G$_{lin}$≥C+C$_{lin}$" is determined in this embodiment.

In detail, G$_{lin}$ is set to such a small value that causes no self-oscillation. After this, G$_{lin}$ is gradually increased, and whether or not the oscillator 41 is oscillating is determined. Alternatively, G$_{lin}$ in a state where the oscillator 41 is self-oscillating is gradually decreased, and whether or not the amplitude of self-oscillation of the oscillator 41 is no longer detected is determined.

Whether or not the oscillator 41 is oscillating is determined as follows. For example, the self-oscillation detection unit 49 may determine that the oscillator 41 is oscillating, in the case where the oscillation displacement x or the oscillation velocity dx/dt changes by a preset threshold or more. Alternatively, the self-oscillation detection unit 49 may compute the frequency spectrum of the oscillation amplitude of the oscillator 41 by, for example, performing a FFT on the oscillation displacement data made up of the oscillation displacement x and, in the case where a spectrum of a single oscillation frequency is generated, determine that the oscillator 41 is oscillating.

In the case where the procedure proceeds to step S320, the computing unit 50 acquires the oscillation limit gain G$_{lin}$*, which is the linear velocity feedback gain when G$_{lin}$≥C+C$_{lin}$, from the self-oscillation detection unit 49. The procedure then proceeds to step S322.

In other words, the computing unit 50 acquires G$_{lin}$ when the oscillator 41 changes from the non-oscillating state to the oscillating state or G$_{lin}$ when the oscillator 41 changes from the oscillating state to the non-oscillating state, as the oscillation limit gain G$_{lin}$*.

In step S322, since G$_{lin}$ and C are known, the computing unit 50 computes the linear viscosity C$_{lin}$ of the measurement object from the expression "G$_{lin}$*=C+C$_{lin}$" obtained by modifying (G$_{lin}$−C−C$_{lin}$) in the expression (24), and stores computed C$_{lin}$ in the memory. The procedure then proceeds to step S324.

In step S324, the gain adjustment unit 54 changes the linear velocity feedback gain G$_{lin}$ by preset Δg2. The procedure then proceeds to step S326.

Here, G$_{lin}$ is changed to change the oscillation amplitude a of the oscillator 41.

In step S326, the computing unit 50 computes the oscillation amplitude a from the oscillation displacement x of the oscillator 41. Since the linear velocity feedback gain G$_{lin}$, the damping constant C, the linear viscosity C$_{lin}$, β, and the nonlinear feedback gain G$_{non}$ are known, the computing unit 50 computes the nonlinear viscosity C$_{non}$ of the measurement object from the expression (24), and stores computed C$_{non}$ in the memory. This completes the process.

(Operation)

The following describes the operation of the viscoelasticity measurement device 140 in this embodiment.

Here, the viscoelasticity measurement device 140 in this embodiment is used for a measurement object fluid, which is a fluid viscoelastic body, to measure the viscoelasticity of the measurement object fluid. A cantilever is used as the oscillator 41, and a piezo element is used as the actuator 46.

Before the measurement, the mass M, the damping constant C, and the spring constant K of the oscillator 41 are precisely measured (or acquired from a spec sheet), and the measured (acquired) mass M, damping constant C, and spring constant K are stored in the memory. Of the mass M, the damping constant C, and the spring constant K stored in the memory, the damping constant C is used in the computation process based on the expression (24) by the computing unit 50.

Next, the gain adjustment unit 54 sets each of the linear velocity feedback gain G$_{lin}$ of the amplifier 45 and the nonlinear feedback gain $G_{non}$ of the amplifier 53 to the initial value (step S300). This starts the measurement.

In the case where a cantilever is used as the oscillator 41, when the nonlinear component of the cantilever and the self-oscillation force of the cantilever are balanced with each other, the oscillation amplitude of the cantilever is kept constant due to the property of the cantilever. The oscillation amplitude a of the oscillator 41 can be reduced by increasing the nonlinear feedback gain $G_{non}$. Thus, the oscillation frequency of the oscillator 41 can be kept at a constant linear natural frequency, regardless of the oscillation amplitude.

Here, the viscosity measurement accuracy can be further improved by decreasing the Reynolds number of the measurement system to maintain laminar flow and suppressing vortex generation caused by the oscillation of the oscillator 41. This can be done by amplitude reduction control that reduces the oscillation amplitude at the time of self-oscillation. Causing the oscillator 41 to oscillate through nonlinear feedback can reduce the amplitude of self-oscillation of the oscillator 41. In this way, vortex generation is suppressed, and laminar flow is maintained to prevent turbulence.

After the measurement starts, the displacement detector 43 detects the displacement x of the oscillator 41, and the oscillation velocity computing unit 44 computes the oscillation velocity dx/dt from the displacement x. The oscillation velocity computing unit 44 supplies the oscillation velocity dx/dt to the amplifier 45 and the multiplier 52. The amplifier 45 multiplies the set linear velocity feedback gain $G_{lin}$ and dx/dt, and supplies the multiplication result $G_{lin} \cdot dx/dt$ to the computing unit 55.

The displacement x is also supplied to the multiplier 51. The multiplier 51 computes $x^2$, and supplies $x^2$ to the multiplier 52. The multiplier 52 multiplies $x^2$ from the multiplier 51 and dx/dt from the oscillation velocity computing unit 44, and supplies the multiplication result $G_{non} \cdot x^2 \cdot dx/dt$ to the computing unit 55.

The computing unit 55 computes $(G_{lin} - G_{non} \cdot x^2) \cdot dx/dt$ by subtracting $G_{non} \cdot x^2 \cdot dx/dt$ from $G_{lin} \cdot dx/dt$, and supplies the computation result to the driver 47 as the feedback control signal Fb.

In the case where, in the initial stage of self-oscillation, the displacement of the oscillator 41 is less than the detection lower limit of the displacement sensor, oscillation of a given frequency is applied preliminarily. In detail, the oscillator 41 is caused to oscillate at a given constant frequency.

The driver 47 generates the drive signal for the piezo element for applying, to the oscillator 41, the force Fv based on $(G_{lin} - G_{non} \cdot x^2) \cdot dx/dt$ received from the computing unit 55, and supplies the generated drive signal to the piezo element. A feedback loop by linear and nonlinear feedback gains is thus formed, and the force Fv is applied to the oscillator 41 in the measurement object fluid. Meanwhile, the displacement signal from the displacement detector 43 is supplied to the frequency counter as needed, and the frequency counter detects the oscillation frequency.

In such an initial drive state, the gain adjustment unit 54 increases the nonlinear feedback gain $G_{non}$ of the amplifier 53 in response to a command signal from the CPU (step S302). This decreases the displacement x of the oscillator 41, and the oscillation amplitude a computed by the computing unit 50. When the oscillation amplitude a falls below the present oscillation threshold, the oscillation amplitude a≈0 (step S304: Yes). The computing unit 50 accordingly acquires the frequency $f_s^*$ at the time from the frequency detection unit 48, and computes the oscillation angular frequency $\omega_s$ ($2\pi f_s^* \beta$) (step S306). Since is now known, the computing unit 50 computes the linear elastic modulus $K_{lin}$ of the measurement object fluid from the expression (25) (step S308). The computing unit 50 stores the computed linear elastic modulus $K_{lin}$ of the measurement object fluid in the memory.

When the linear elastic modulus $K_{lin}$ is computed, the viscoelasticity measurement device 140 changes the nonlinear feedback gain $G_{non}$ by preset $\Delta g1$ by the gain adjustment unit 54 (step S310). Since the nonlinear feedback gain $G_{non}$ has become relatively large, the current $G_{non}$ is decreased only by $\Delta g1$.

As a result, the oscillation amplitude a changes (the oscillation amplitude a is no longer about equal to 0), and the computing unit 50 computes the oscillation amplitude a from the oscillation displacement x (step S312). When the oscillation amplitude a changes, $\omega_s$ shown in the expression (26) changes, and a component other than β is generated. The computing unit 50 acquires the oscillation frequency $\omega_s$ at the time from the frequency detection unit 48, and computes the oscillation angular frequency $\omega_s$. Since β, the oscillation amplitude a, and the oscillation frequency $\omega_s$ are now known, the computing unit 50 computes the nonlinear elastic modulus $K_{non}$ of the measurement object fluid based on the expression (26) (step S314). The computing unit 50 stores the computed nonlinear elastic modulus $K_{non}$ of the measurement object fluid in the memory.

When the nonlinear elastic modulus $K_{non}$ is computed, the viscoelasticity measurement device 140 changes the linear velocity feedback gain $G_{lin}$ by the gain adjustment unit 54 (step S316). Here, the linear velocity feedback gain $G_{lin}$ is first set to a relatively small value, and then increased by preset increment $\Delta g$ until the oscillation limit gain is reached.

The self-oscillation detection unit 49 compares the oscillation displacement x after $G_{lin}$ is increased, with a preset displacement threshold. In the case of determining that the displacement x is greater than or equal to the displacement threshold, the self-oscillation detection unit 49 determines that $G_{lin} \geq C + C_{lin}$. In the case of determining that the displacement x is less than the displacement threshold, the self-oscillation detection unit 49 determines not that $G_{lin} \geq C + C_{lin}$.

In the case where the self-oscillation detection unit 49 determines that $G_{lin} \geq C + C_{lin}$ (step S318: Yes), the self-oscillation detection unit 49 acquires this $G_{lin}$ as the oscillation limit gain $G_{lin}^*$, and supplies it to the computing unit 50 (step S320).

When $G_{lin}$ is the oscillation limit gain $G_{lin}^*$, $G_{lin}^* \approx C + C_{lin}$. The computing unit 50 accordingly computes the linear viscosity $C_{lin}$ of the measurement object fluid, from known $G_{lin}^*$ and the damping constant C of the oscillator 41 stored in the memory (step S322). The computing unit 50 stores the computed linear viscosity $C_{lin}$ of the measurement object fluid in the memory.

When the linear viscosity $C_{lin}$ is computed, the viscoelasticity measurement device 140 changes the linear velocity feedback gain $G_{lin}$ by preset $\Delta g2$ by the gain adjustment unit 54 (step S324). This changes the oscillation amplitude a of the oscillator 41, and the computing unit 50 computes the oscillation amplitude a from the displacement x of the oscillator 41. Since the oscillation amplitude a, the linear velocity feedback gain $G_{lin}$, β, the damping constant C, the linear viscosity $C_{lin}$, and the nonlinear feedback gain $G_{non}$ are known, the computing unit 50 computes the nonlinear viscosity $C_{non}$ based on the expression (24) (step S326). The computing unit 50 stores the computed nonlinear viscosity $C_{non}$ of the measurement object fluid in the memory.

As described above, the viscoelasticity measurement method and the viscoelasticity measurement device 140 in this embodiment enable the following. In a state where the oscillator 41 with the mass M is in contact with the viscoelastic body, the force Fv is applied to the oscillator 41 to cause the oscillator 41 to self-oscillate.

In addition, the actuator for applying the force Fv to the oscillator is driven and feedback-controlled by the linear velocity feedback control signal obtained by multiplying the linear velocity feedback gain $G_{lin}$ and the oscillation velocity dx/dt and the nonlinear feedback control signal obtained by multiplying the nonlinear feedback gain $G_{non}$, the square of the displacement x, and the oscillation velocity dx/dt.

The linear velocity feedback gain $G_{lin}$ and the nonlinear feedback gain $G_{non}$ are controlled to measure the linear viscosity $C_{lin}$, the nonlinear viscosity $C_{non}$, the linear elastic modulus $K_{lin}$, and the nonlinear elastic modulus $K_{non}$ of the measurement object, based on the expressions (23) to (25).

This enables measurement of not only the linear viscosity and linear elasticity of the material of the measurement object but also the nonlinear viscosity and nonlinear elasticity of the material of the measurement object. In addition, the time variation of viscosity can be measured in real time.

Furthermore, the amplitude of self-oscillation of the oscillator 41 can be reduced by nonlinear feedback control. Hence, in the case where the measurement object is a fluid, vortex generation is suppressed, and laminar flow is maintained to prevent turbulence.

In the foregoing embodiment, the amplifier 45, the multipliers 51 and 52, the amplifier 53, the computing unit 55, and the driver 47 constitute a feedback control unit, the oscillation velocity computing unit 44 constitutes an oscillation velocity detection unit, the displacement sensor 42, the displacement detector 43, and the frequency detection unit 48 constitute a physical quantity measurement unit, and the computing unit 50 constitutes a viscoelasticity computing unit.

In the foregoing embodiment, steps S300, S302, S310, S316, and S324 correspond to a gain adjustment step, and steps S306, S312, and S320 correspond to a physical quantity measurement step.

In the foregoing embodiment, steps S308, S314, S322, and S326 correspond to a step of detecting whether or not the oscillator is self-oscillating, and step S308 corresponds to a viscoelasticity computing step.

(Modifications)

In Embodiment 1 described above, the structure in which a force in the shear deformation direction is applied to a linear elastic body as a measurement object is described as an example. However, the present invention is not limited to this structure.

For example, a force of deforming in another direction such as the tensile direction or the compression direction may be applied to the linear elastic body.

In Embodiment 1 described above, a thin film solid material is used as the linear elastic body as an example. However, the present invention is not limited to solid materials, and is also applicable to other linear elastic bodies such as fluids.

In Embodiment 1 described above, the gain adjustment unit is provided to automatically change the linear velocity feedback gain $G_{lin}$. However, the present invention is not limited to this structure, and the linear velocity feedback gain $G_{lin}$ may be manually changed.

In Embodiment 2 described above, the present invention is applied to a cone and plate rheometer as an example. However, the present invention is not limited to this structure.

For example, the present invention is also applicable to viscoelasticity measurement devices such as a tensile tester and a plastometer.

In Embodiment 2 described above, the present invention is used to specify the rheological properties as an example. The present invention is also applicable as a method of measuring the oscillation properties of a structure such as a car, a robot, or a building.

In Embodiment 2 described above, the frequency adjustment unit 25 is provided to automatically change the passing frequency band (specific frequency) of the bandpass filter 24. However, the present invention is not limited to this structure, and the passing frequency band of the bandpass filter 24 may be manually changed.

In Embodiment 2 described above, the gain adjustment unit 27 is provided to automatically change the linear velocity feedback gain $G_{lin}$ of the amplifier 28. However, the present invention is not limited to this structure, and the linear velocity feedback gain $G_{lin}$ may be manually changed.

In Embodiment 3 described above, a cantilever is used as the oscillator as an example. However, the present invention is not limited to this structure.

For example, the oscillator may be a conventional oscillatory viscometer, rotating cylinder, parallel plate, or the like.

In Embodiment 3 described above, the feedback control system uses digital technology. However, the present invention is not limited to this structure, and analog technology may be used.

In Embodiment 3 described above, the measurement object is a fluid having both viscosity and elasticity as an example. However, the present invention is not limited to fluids, and is also applicable to semisolids or solids such as a thin film material.

In Embodiment 3 described above, the gain adjustment unit is provided to automatically change the linear velocity feedback gain $G_{lin}$ and the nonlinear feedback gain $G_{non}$. However, the present invention is not limited to this structure, and the linear velocity feedback gain $G_{lin}$ and the nonlinear feedback gain $G_{non}$ may be manually changed.

Though the embodiments described above are preferred examples of the present invention and various technically preferable limitations are given, the scope of the present invention is not limited to these embodiments unless there is description to the effect that the present invention is particularly limited. The drawings used in the above description are schematic diagrams where members and parts are not to actual vertical and horizontal scale, for convenience's sake.

The present invention is not limited to the embodiments described above, and modifications and improvements are included in the present invention within the scope for achieving the object of the present invention.

The present invention achieves accurate and stable linear elastic modulus measurement even in the case where damping due to viscous stress is large. This technique enables accurate elastic modulus measurement of a viscoelastic body when used in a rheometer, and is useful for research and development of plastic goods, foods, drugs, and so on. A device for accurately measuring the hardness of an internal organ and the like can be realized, too.

The present invention can measure a clear viscoelastic spectrum even in the case where the viscoelasticity of a viscoelastic body cannot be modeled by a simple mechanical model. This technique enables accurate elastic modulus measurement of a viscoelastic body when used in a rheometer, and is useful for research and development of plastic goods, foods, drugs, and so on. This technique is also useful as a method of measuring the oscillation properties of a structure such as a car, a robot, or a building.

Though Embodiment 2 described above is limited to the measurement of a viscoelastic body, it is also possible to clearly measure the ratios of a plurality of spring constants, viscous moduli, and added masses, in a complex system that needs to be modeled by a mechanical system having a plurality of spring elements and viscous elements.

The present invention can measure not only the linear viscosity and linear elasticity of a viscoelastic body as a measurement object but also the nonlinear viscosity and nonlinear elasticity of the viscoelastic body.

Food companies put particular importance on precise viscosity measurement and management, to obtain scientific indicators of quality, taste, and chewing sense of developed foods.

Chemical measuring instrument manufacturers aim to improve the viscosity measurement accuracy and usability, but have not yet invented a novel measurement principle that can be a breakthrough to higher accuracy.

The present invention is also applicable to, for example, the automobile field seeking to improve fuel economy by local real time measurement in engines.

While the present invention has been described with respect to a limited number of embodiments, those skilled in the art, having benefit of this disclosure, will appreciate that the embodiments may be modified which do not depart from the scope of the disclosure as described herein.

The invention claimed is:

1. A linear elastic modulus measurement method using a linear elastic modulus measurement device, comprising:
   an oscillator that is brought into contact with a viscoelastic measurement object;
   an actuator for causing the oscillator to self-oscillate;
   an oscillation velocity detection unit for detecting an oscillation velocity of the oscillator;
   a feedback control unit for positively feeding back the oscillation velocity detected by the oscillation velocity detection unit, to feedback control the actuator by a feedback control signal defined as:

$Fs=G_{lin}\cdot(dx/dt)$;

where Fs is the feedback control signal, $G_{lin}$ is a linear velocity feedback gain, which is a positive value, x is a displacement of the oscillator, and dx/dt is the oscillation velocity of the oscillator;
   a displacement detection unit for detecting the displacement of the oscillator based on sensor output from a displacement sensor;
   a frequency detection unit for detecting an oscillation waveform based on the displacement of the oscillator supplied from the displacement detector; and
   a memory for storing a mass of the oscillator, wherein the linear elastic modulus measurement device causes the viscoelastic measurement object to self-oscillate by a change of the linear velocity feedback gain, and the linear elastic modulus method comprises:
   preliminarily causing the oscillator to oscillate at a constant frequency, where an amount of the displacement of the oscillator in an initial stage when the oscillator starts self-oscillation is less than a detection lower limit of the displacement detection unit;
   changing the linear velocity feedback gain in the feedback control unit by a preset amount Δg, wherein the preset amount Δg is set to a value that allows the oscillation frequency to be detected from the displacement of the oscillator, the linear velocity feedback gain is kept at Glin+Δg, and the changing of the linear velocity feedback gain results in external disturbances to the viscoelastic measurement object;
   detecting whether or not the oscillator is self-oscillating based on the oscillation velocity detected by the oscillator velocity detection unit; and
   computing the linear elastic modulus $K_{lin}$ of the viscoelastic measurement object as:

$Klin=\omega_s^2 \times M$, where $\omega_s=2\pi \times f_s$, M is a mass of the oscillator, and $f_s$ is an oscillation frequency when the oscillator velocity detection unit detects that the oscillator is self-oscillating,
   wherein the linear elastic modulus as computed is independent of the external disturbances to the viscoelastic measurement object.

2. The method according to claim 1, further comprising:
   detecting the displacement of the oscillator using the displacement sensor;
   extracting, using a specific frequency component extraction unit, a signal component of a specific frequency from a displacement signal output from the displacement sensor; and
   changing the specific frequency used when the specific frequency component extraction unit extracts the signal component; wherein
   detecting the oscillation velocity of the oscillator comprises detecting the oscillation velocity based on the signal component of the specific frequency extracted by the specific frequency component extraction unit;
   changing the linear velocity feedback gain in the feedback control comprises changing the linear velocity feedback gain for the changed specific frequency, and
   detecting whether or not the oscillator is self-oscillating occurs each time the feedback control is performed using the changed linear velocity feedback gain.

3. The method according to claim 2, further comprising:
   generating a frequency spectrum of viscoelasticity indicating a relation between an inverse of the linear velocity feedback gain and an oscillation angular frequency corresponding to each specific frequency when self-oscillating of the oscillator is detected.

4. The method according to claim 2, wherein the specific frequency component extraction unit includes a bandpass filter.

5. A linear elastic modulus measurement device comprising:
   an oscillator that is brought into contact with a viscoelastic measurement object;
   an actuator for causing the oscillator to self-oscillate;
   an oscillation velocity detection unit for detecting an oscillation velocity of the oscillator;
   a feedback control unit for positively feeding back the oscillation velocity detected by the oscillation velocity detection unit, to feedback-control the actuator by a feedback control signal defined as:

$Fs=G_{lin}\cdot(dx/dt)$;

where Fs is the feedback control signal, $G_{lin}$ is a linear velocity feedback gain, which is a positive value, x is a displacement of the oscillator, and dx/dt is the oscillation velocity of the oscillator;

a displacement detection unit for detecting the displacement of the oscillator based on sensor output from a displacement sensor, wherein the displacement detection unit has a detection lower limit;

a frequency detection unit for detecting an oscillation waveform based on the displacement of the oscillator supplied from the displacement detector;

a memory for storing a mass of the oscillator;

a gain adjustment unit for changing the linear velocity feedback gain in the feedback control unit by a preset amount $\Delta g$ after preliminarily causing the oscillator to oscillate at a constant frequency, where an amount of the displacement of the oscillator in an initial stage when the oscillator starts self-oscillation is less than the detection lower limit of the displacement detection unit, the preset amount $\Delta g$ is set to a value that allows the oscillation frequency to be detected from the displacement of the oscillator, the linear velocity feedback gain is kept at Glin+$\Delta$g, and the changing of the linear velocity feedback gain results in external disturbances to the viscoelastic measurement object;

a self-oscillation detection unit for detecting whether or not the oscillator is self-oscillating based on the oscillation velocity detected by the oscillator velocity detection unit; and a linear elastic modulus computing unit for computing a linear elastic modulus $K_{lin}$ of the viscoelastic measurement object as:

$$Klin=\omega_s^2 \times M,$$

where $\omega_s=2\pi \times f_s$, M is a mass of the oscillator, and $f_s$ is an oscillation frequency when the self-oscillation detection unit determines that self-oscillating of the oscillator is detected, wherein the linear elastic modulus as computed is independent of the external disturbances to the viscoelastic measurement object.

6. The device according to claim 5, further comprising:

a specific frequency component extraction unit for extracting a signal component of a specific frequency from a displacement signal output from the displacement sensor; wherein:

the oscillation velocity detection unit detects the oscillation velocity of the oscillator based on a displacement signal component of the specific frequency extracted by the specific frequency component extraction unit, the specific frequency adjustment unit changes the specific frequency used when the specific frequency component extraction unit extracts the signal component, the gain adjustment unit changes the linear velocity feedback gain in the feedback control for the changed specific frequency, and the self-oscillation detection unit detects whether or not the oscillator is self-oscillating each time the feedback control is performed using the changed linear velocity feedback gain, the device further comprising:

a viscoelasticity measurement unit for measuring the linear velocity feedback gain when self-oscillating of the oscillator is detected.

* * * * *